United States Patent [19]

Clark et al.

[11] 4,144,341

[45] Mar. 13, 1979

[54] IMIDAZO PYRIDINE-2-ONES AND PHARMACEUTICAL COMPOSITIONS AND METHODS OF TREATMENT UTILIZING SAME

[75] Inventors: Robert L. Clark, Woodbridge; Arsenio A. Pessolano, Colonia; Tsung-Ying Shen, Westfield, all of N.J.

[73] Assignee: Merck & Co., Inc., Rahway, N.J.

[21] Appl. No.: 853,975

[22] Filed: Nov. 22, 1977

Related U.S. Application Data

[63] Continuation-in-part of Ser. No. 670,798, Mar. 26, 1976, abandoned, which is a continuation-in-part of Ser. No. 601,672, May 28, 1975, abandoned.

[51] Int. Cl.$^2$ .................. A61K 31/435; C07D 471/04

[52] U.S. Cl. ..................................... 424/256; 546/84; 546/118

[58] Field of Search .................... 260/295 K, 295.5 B; 424/256

[56] References Cited

U.S. PATENT DOCUMENTS 3,719,683  3/1973  Robinson et al. ............. 260/294.8 C

*Primary Examiner*—Alan L. Rotman
*Attorney, Agent, or Firm*—Raymond M. Speer; Mario A. Monaco

[57] ABSTRACT

1,3-Dihydroimidazo[4,5-b]pyridin-2-ones and corresponding thiones have utility as analgesic, antipyretic and antiinflammatory agents. They are generally prepared by treatment of a 2,3-diaminopyridine with phosgene or thiophosgene followed by further substitution if desired.

20 Claims, No Drawings

IMIDAZO PYRIDINE-2-ONES AND PHARMACEUTICAL COMPOSITIONS AND METHODS OF TREATMENT UTILIZING SAME

This application is a continuation-in-part of prior co-pending application Ser. No. 670,798, filed Mar. 26, 1976 and now abandoned, which in turn was a continuation-in-part of application Ser. No. 601,672, filed May 28, 1975, now abandoned.

This invention is concerned with novel 1,3-dihydroimidiazo[4,5-b]pyridin-2-ones and in addition, these novel compounds and 1,3-dihydroimidazo[4,5-b]pyridin-2-thiones as regards processes for their preparation, pharmaceutical compositions comprising the compounds as active ingredient, and the method of treating fever and/or pain and/or inflammation with the compounds and compositions.

In particular, it is concerned with the novel compounds of the following structural formula:

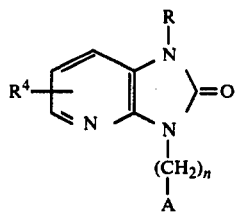

wherein
n is 0-3,
R is (1) hydrogen,
  (2) lower alkyl, especially $C_{1-7}$ alkyl, either straight or branched chain and either unsubstituted or substituted with one or more groups such as
    (a) phenyl,
    (b) lower cycloalkyl, especially $C_{3-6}$-cycloalkyl,
    (c) lower alkoxy, especially $C_{1-5}$ alkoxy,
    (d) acetoxy,
    (e) epoxy,
    (f) hydroxy,
    (g) lower alkoxycarbonyl, especially $C_{1-3}$ alkoxycarbonyl,

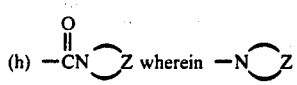

is a 5-6 membered heterocycle, especially morpholinyl,
  (3) lower alkenyl, especially $C_{2-6}$ alkenyl such as allyl, allenyl, and butadienyl, either straight or branched chain and either unsubstituted or substituted with one or more groups such as
    (a) halo, such as chloro, or
    (b) phenyl,
  (4) lower alkynyl, especially $C_{2-5}$ alkynyl,
  (5) lower cycloalkylcarbonyl, especially $C_{3-6}$ cycloalkylcarbonyl,
  (6) lower alkanoyl, especially $C_{2-5}$ alkanoyl,
  (7) carbamoyl, either unsubstituted or substituted with loweralkyl, especially $C_{1-7}$ alkyl,
  (8) lower alkoxycarbonyl, especially $C_{1-3}$ alkoxycarbonyl,
  (9) phenacyl,
  (10) phenylsulfonyl, either unsubstituted or substituted with halo, especially fluoro
  (11) trifluoromethylsulfonyl,
  (12) 5-6 membered heterocycle, especially thiazolinyl,
  (13) lower cycloalkyl, especially $C_{4-7}$ cycloalkyl, such as cyclopentyl, A is (1) pyridyl, either unsubstituted or substituted with lower alkyl, especially $C_{1-3}$ alkyl,
  (2) lower cycloalkyl, especially $C_{3-6}$cycloalkyl, (3) 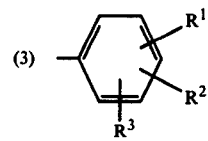

wherein $R^1$ and $R^2$ are the same or different and each is
  (a) hydrogen,
  (b) lower alkoxy, especially $C_{1-3}$ alkoxy, either straight or branched chain,
  (c) lower alkyl, especially $C_{1-5}$ alkyl,
  (d) halo, such as chloro, bromo, or fluoro,
  (e) trifluoromethyl,
  (f) amino, either unsubstituted or substituted with lower alkyl, especially $C_{1-5}$ alkyl,
  (g) phenoxy, or
  (h) cyano,
$R^1$ and $R^2$ on adjacent carbon atoms taken together represent (a) 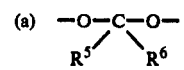

wherein $R^5$ and $R^6$ are hydrogen or lower alkyl, especially $C_{1-3}$ alkyl,
(b) $-O-(CH_2)_m-O-$ wherein m is 1-3,
(c) $-CH_2-O-CH_2-$ (d) 

where $R^5$ and $R^6$ are hydrogen or lower alkyl, especially $C_{1-3}$ alkyl,
(e) $-(CH_2)_3-$
$R^3$ is (a) hydrogen,
  (b) lower alkyl, especially $C_{1-3}$ alkyl, either straight or branched chain, or (c) lower alkoxy, especially $C_{1-3}$ alkoxy,
$R^4$ is (1) hydrogen,
  (2) 5- or 6- lower alkyl, especially $C_{1-5}$alkyl,
  (3) 5- or 6- nitro
  (4) 5- or 6- amino
  (5) 5- or 6- halo, especially fluoro, or
  (6) 5- or 6-lower alkoxy carbonylamino especially $C_{1-5}$ lower alkoxy carbonylamino.

A preferred group of the novel compounds are those having the following formula:

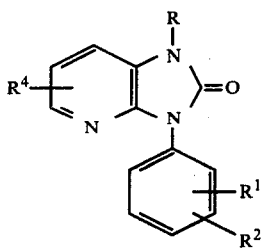

wherein
- R is hydrogen; $C_{1-7}$ alkyl, especially $C_{1-4}$ alkyl; $C_{2-6}$ alkenyl, especially $C_{2-5}$ alkenyl; $C_{1-7}$ especially $C_{1-4}$ alkyl substituted with $C_{3-6}$ cycloalkyl, $C_{1-5}$ alkoxy, or hydroxy; or $C_{4-7}$ cycloalkyl;
- $R^1$ and $R^2$ are hydrogen; fluoro; $C_{1-5}$ alkyl; or —O—$CH_2$—O— attached to adjacent carbon atoms; and $R^4$ is hydrogen; 5- or 6- fluoro; 5- or 6- chloro; or 5- or 6- $C_{1-5}$ alkoxy carbonylamino.

Preferred specific compounds within the above preferred group are the following:

1-allyl-1,3-dihydro-3-(3,4-methylenedioxyphenyl) imidazo[4,5-b]pyridin-2-one 1,3-dihydro-3-(3,4-methylenedioxyphenyl) imidazo [4,5-b] pyridin-2-one 1-isopropyl-1,3-dihydro-3-(3,4-methylenedioxyphenyl) -imidazo[4,5-b]pyridin-2- one 1-butyl-1,3-dihydro-3-(3,4-methylenedioxyphenyl) imidazo[4,5-b]pyridin-2-one 6-ethoxycarbonylamino-1-n-propyl-1,3-dihydro-3-(3,4-methylenedioxyphenyl)imidazo[4,5-b]pyridin-2-one 6-fluoro-1-n-propyl-1,3-dihydro-3-(3,4-methylenedioxyphenyl)imidazo[4,5-b]pyridin-2-one 5-ethoxycarbonylamino-1-allyl-1,3-dihydro-3-(3,4-methylenedioxyphenyl)imidazo[4,5-b]pyridin-2-one 5-fluoro-1,3-dihydro-3-(3,4-methylenedioxphenyl) imidazo[4,5-b]pyridin-2-one 5-fluoro-1-allyl-1,3-dihydro-3-(3,4-methylenedioxyphenyl)imidazo-[4,5-b]pyridin-2-one 1-n-propyl-1,3-dihydro-3-(3,4-methylenedioxyphenyl) imidazo[4,5-b]pyridin-2-one 1-allyl-1,3-dihydroimidazo[4,5-b]pyridin-2-one 1-methyl-1,3-dihydro-3-(3,4-methylenedioxyphenyl) imidazo[4,5-b]pyridin-2-one 1-ethyl-1,3-dihydro-3-(3,4-methylenedioxphenyl) imidazo[4,5-b]pyridin-2-one 1,3-dihydro-3-(4-methylphenyl)imidazo[4,5-b]pyridin-2-one 1-cyclopropylmethyl-1,3-dihydro-3-(3,4-methylenedioxyphenyl)imidazo[4,5-b]pyridin-2-one 1-hydroxyethyl-1,3-dihydro-3-(3,4-methylenedioxyphenyl)imidazo[4,5-b]pyridin-2-one 1-cyclopentyl-1,3-dihydro-3-(3,4-methylenedioxyphenyl) imidazo[4,5-b]pyridin-2-one 1-methoxymethyl-1,3-dihydro-3-(3,4-methylenedioxyphenyl) imidazo[4,5-b]pyridin-2-one 5-chloro-1-allyl-1,3-dihydro-3-(3,4-methylenedioxyphenyl) imidazo[4,5-b]pyridin-2-one The above preferred group of the novel compounds comprises two smaller groups of more preferred compounds. The first of these groups is of compounds having the formula:

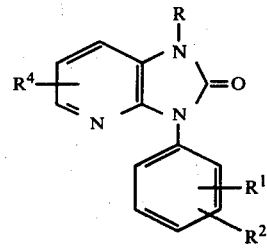

wherein R is hydrogen, $C_{1-7}$ alkyl, especially $C_{1-4}$ alkyl, or $C_{2-6}$ alkenyl, especially $C_{2-5}$ alkenyl; $R^1$ and $R^2$ are hydrogen or fluoro, or taken together represent —O—$CH_2$—O— attached to adjacent carbon atoms; and $R^4$ is hydrogen, 5- or 6- fluoro, or 5- or 6- lower alkoxy carbonylamino.

The second of these groups is of compounds having the formula:

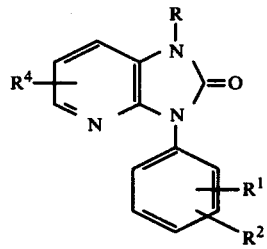

wherein
- R is hydrogen, $C_{1-7}$ alkyl, especially $C_{1-4}$alkyl; $C_{2-6}$alkenyl, especially $C_{2-5}$ alkenyl; $C_{1-7}$ especially $C_{1-4}$ alkyl substituted with $C_{3-6}$ cycloalkyl, $C_{1-5}$ alkoxy, or hydroxy; or $C_{4-7}$ cycloalkyl;
- $R^1$ and $R^2$ are hydrogen; fluoro; $C_{1-5}$ alkyl; or —O—$CH_2$—O— attached to adjacent carbon atoms; and
- $R^4$ is hydrogen; 5- or 6- chloro; or 5- or 6- $C_{1-5}$ alkoxy carbonylamino; provided that, R and $R^4$ may only both be hydrogen when at least one of $R^1$ and $R^2$ is $C_{1-5}$ alkyl, and that, when R is hydrogen, $C_{1-7}$ especially $C_{1-4}$ alkyl, or $C_{2-6}$ especially $C_{2-5}$ alkenyl, $R^4$ is 5- or 6- chloro.

Another preferred group of the novel compounds are those having the following formula:

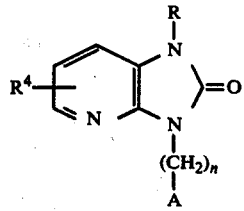

wherein
- n is 0–3;
- R is (1) hydrogen; (2) $C_{1-7}$ especially $C_{1-4}$ alkyl substituted with one or more groups selected from
  - (a) phenyl
  - (b) epoxy
  - (c) lower alkoxycarbonyl,
- (3) $C_{2-6}$ especially $C_{2-5}$ alkenyl substituted with a group selected from
  - (a) halo (b) phenyl,
(4) lower alkynyl,
(5) lower cycloalkylcarbonyl,
(6) lower alkanoyl,
(7) carbamoyl or lower alkylcarbamoyl,
(8) lower alkoxycarbonyl,
(9) phenacyl;
A is (1) pyridyl, or $C_{1-3}$ alkylpyridyl,
(2) lower cycloalkyl, or

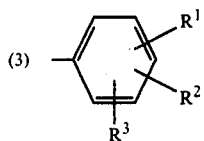

wherein $R^1$ and $R^2$ are hydrogen and fluoro, both fluoro, or taken together on adjacent carbon atoms are

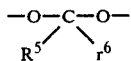

where $R^5$ and $R^6$ are hydrogen or $C_{1-4}$ alkyl, and $R^3$ is hydrogen, lower alkyl, or lower alkoxy; and $R^4$ is (1) hydrogen,
(2) 5- or 6- lower alkyl, especially $C_{1-5}$ alkyl,
(3) 5- or 6- nitro,
(4) 5- or 6- amino, or
(5) 5- or 6- bromo;
provided that, when n is O, R and $R^4$ may not both be hydrogen.

Yet another preferred group of the novel compounds are those having the following formula:

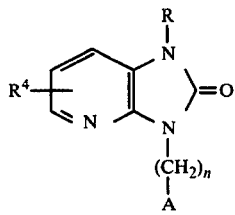

wherein
n is 0–3;
R is (1) hydrogen,
(2) $C_{1-7}$ especially $C_{1-4}$ alkyl or alkyl substituted with one or more groups selected from
(a) phenyl,
(b) lower cycloalkyl,
(c) epoxy,
(d) acetoxy
(e) hydroxy,
(f) lower alkoxycarbonyl,
(3) $C_{2-6}$ especially $C_{2-5}$ alkenyl or alkenyl substituted with a group selected from
(a) a halo,
(b) a phenyl,
(4) lower alkynyl,
(5) lower cycloalkylcarbonyl,
(6) lower alkanoyl,
(7) carbamoyl or lower alkylcarbamoyl,
(8) lower alkoxycarbonyl,
(9) phenacyl;

A is (1) pyridyl, or $C_{1-3}$ alkylpyridyl,
(2) lower cycloalkyl,

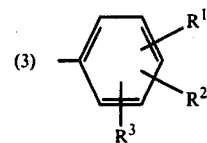

wherein $R^1$ and $R^2$ are the same or different and each is
(a) hydrogen
(b) lower alkoxy,
(c) lower alkyl,
(d) bromo or chloro,
(e) trifluoromethyl,
(f) amino, or amino substituted with lower alkyl,
(g) phenoxy,
(h) cyano, or
$R^1$ and $R^2$ on adjacent carbon atoms taken together are
(a) —O—$(CH_2)_m$—O— wherein m is 1–3,
(b) —$CH_2$—O—$CH_2$—,

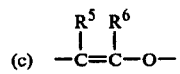

where $R^5$ and $R^6$ are hydrogen or lower alkyl,
(d) — $(CH_2)_3$—, and
$R^3$ is (1) hydrogen,
(2) lower alkyl, or
(3) lower alkoxy; and
$R^4$ is (1) hydrogen,
(2) 5- or 6- lower alkyl, especially $C_{1-5}$ alkyl,
(3) 5- or 6- nitro,
(4) 5- or 6- amino,
(5) 5- or 6- halo, especially fluoro,
(6) 5- or 6- lower alkoxy carbonylamino, especially $C_{1-5}$ alkoxy carbonylamino;
provided that, when n is O, at lest one of $R^1$ and $R^2$, $R^3$ and $R^4$ is other than hydrogen, except in such case when only $R^4$ is other than hydrogen, it may not be 5- or 6-halo or 5- or 6- lower especially $C_{1-5}$ alkoxy carbonylamino.

Another group of novel compounds are those of formula:

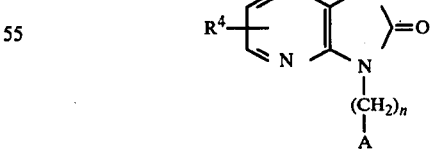

wherein R is $C_{1-7}$ alkyl substituted with

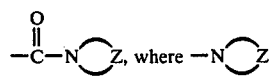

is a 5-6 membered heterocycle; or, 5-6 membered heterocycle;

and n, A, and $R^4$ have the same meaning as set out above under the broadest description of the novel compounds of the present invention.

Yet another group of novel compounds are those of formula:

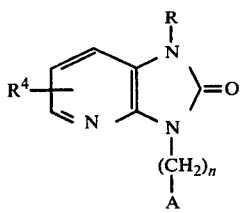

wherein R is phenylsulfonyl, halophenylsulfonyl, or trifluoromethylsulfonyl;

and n, A, and $R^4$ have the same meaning as set out above under the broadest description of the novel compounds of the present invention.

As already indicated above, in addition to the novel imidazo [4,5-b] pyridin-2-ones described above, the present invention is concerned with utilization of these novel compounds as well as certain imidazo [4,5-b] pyridin2-thiones as the active ingredient in pharmaceutical compositions, and in the method treating fever and/or pain and/pr inflammation with the compounds and compositions.

The imidazo [4,5-b] pyridin-2-thiones which are useful in the pharmaceutical compositions and method of treatment of the present invention have the following structural formula:

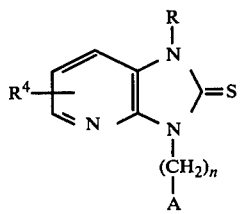

wherein n, R, A, and $R^4$ have the same meaning as set out above under the broadest description of the novel imidazo [4,5--b] pyridin-2-ones.

In addition to the novel imidazo [4,5-b]pyridin2-ones, the present invention is also concerned with the novel compound 1,3-dihydro-3-(3,4-methylenedioxyphenyl-)imidazo[4,5-b]pyridin-2-thione.

The novel 1,3-dihydroimidazo[4,5-b]pyridines of this ivention can be prepared by a variety of procedures.

One procedure is depicted by the following equation:

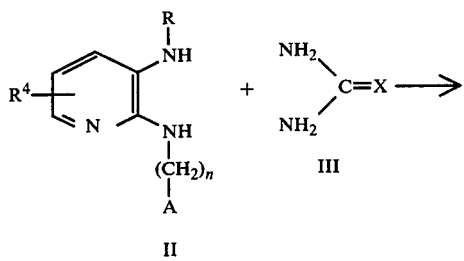

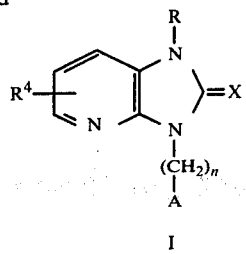

wherein X, n, R, A, and $R^4$ are as previously defined. The process comprises mixing about 1 to 5 times the stoichiometric amount of Compound III with Compound II and heating the mixture at least at its fusion point for 10 to 60 minutes, preferably about 30 minutes. The product can be isolated by a variety of standard procedures, but it is convenient to extract the cooled mixture with dilute alkali such as 2-4 N sodium hydroxide solution, and then acidify the extract with a weak acid such as acetic acid which causes precipitation of the desired product.

A second procedure is represented by the following equation:

$$R^4 \underset{N}{\overset{R \quad X}{\underset{|}{N}-\overset{\|}{C}-NH(CH_2)_n-A}} \xrightarrow[Cu]{(metal)_2CO_3}$$

IV $$R^4 \quad \rightarrow \quad I \quad (CH_2)_n \quad A \quad =X$$

I where X, n, R, $R^4$ and A are as previously defined, Hal is a halogen atom preferably chloro, and metal is an alkali metal, preferably Na or K. The process comprises heating at 140°–200° C. for 2–6 hours a mixture of Compound IV in an inert solvent such as dimethyl formamide, diglyme or the like, an approximately equimolar amount of an alkali metal carbonate such as sodium carbonate or potassium carbonate and a catalytic amount of powdered copper. The product can be isolated by a variety of standard procedures but it is convenient to evaporate the solvent, and further purify the product as described above.

A preferred procedure is represented by the following equation:

$$R^4 \underset{N}{\overset{R}{\underset{NH}{\underset{|}{NH}}}} \xrightarrow{CXCl_2}$$

V

-continued

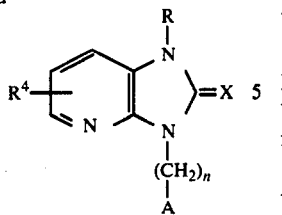

wherein X, n, R, A and $R^4$ are as previously defined. The process comprises dissolving Compound V in a solvent, adding to the stirred solution at least 1 molar equivalent of $CXCl_2$ (phosgene or thiophosgene) over 10-13 minutes (in practice gaseous phosgene is bubbled into the solution until reaction is complete), and permtting the reaction mixture to stand at room temperature for 2-24 hours. The temperature is not critical and room temperature is merely most convenient. Usually the ring closure is conducted in aqueous solution in the presence of an acid. This procedure is dictated somewhat by the unstable nature of the diamino compound, V, which is frequently not isolated but rather held in aqueous acid solution. However, where the diamino compound is stable as the free base, it can equally well be ring closed with phosgene or thiophosgene in an organic solvent such as benzene, or the like.

Each of the above synthetic schemes has been described with the substituent R on the starting material, having a variety of definitions. In actual practice, because of difficulties in synthesizing the starting materials, it is found more convenient to perform the ring closure reactions with starting materials where R represens hydrogen, followed, where desired, by substitution of the $N_1$ hydrogen to provide products carrying the other R substituents.

The novel compounds in which R is acyl, either carboxy acyl or sulfonyl acyl, or alkyl or substituted alkyl, are readily prepared by adding one of the novel compounds wherein R is hydrogen, to an inert solvent such as acetone, methyl ethyl ketone, or the like, and with stirring adding a molar equivalent of powdered KOH and an approximately molar equivalent to slight excess of the compound R-hal such as

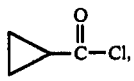

$CH_3SO_2Cl$, $CH_3I$

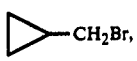

$CH_2=CH-CH_2Br$, or the like. Stirring is continued at a temperature from room temperature to reflux until reaction is complete (1-4 hours). The 1-alkanoyl compounds are also conveniently prepared by adding one of the novel compounds, wherein R is hydrogen, to an excess of the appropriate anhydride such as acetic anhydride and warming at 50°-100° C. for 3-24 hours. The product is isolated by standard procedures well known to one skilled in the art.

Where R is hydroxymethyl, the 1-unsubstituted compound is treated with formaldehyde at steam bath temperature for 0.5-3 hours.

Where R is —CONH-alkyl, the 1-unsubstituted compound is treated with an alkyl isocyanate in an inert solvent such as dimethoxyethane at reflux temperature until solution occurs.

Where R is thiazolinyl, the 1-unsubstituted compound is treated with sodium hydride at room temperature and 2-chloroethylisothiocyanate at reflux in an inert solvent such as dimethoxyethane.

Catalytic reduction of a 1-phenacyl compound yields the corresponding 1-(2-hydroxy-2-phenylethyl) compound.

Preparation of the 1-lower alkoxycarbonylmethyl compound by alkylation as described previously usually results in production of some 1-acetic acid compound. Treatment of this with thionyl chloride yields the corresponding 1-acetyl chloride which on treatment with a nitrogen heterocycle such as morpholine yields a compound substituted in the 1-position such as

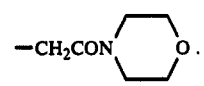

Alkylation of the 1-unsubstituted compounds normally is conducted through the influence of a base. Where the alkylating reagent is 2,3-dichloropropene, not only does it alkylate to yield a 1-(2-chloroallyl compound but it also suffers dehydrohalogenation to a 1-allenyl substituent.

An additional and preferred synthesis of the 2-thiones is depicted by the following equation:

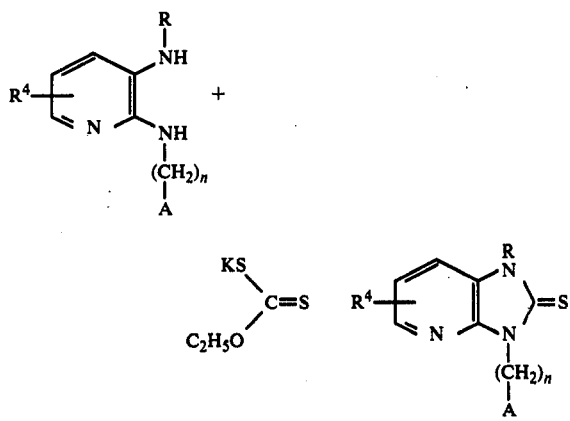

The process comprises mixing approximately equimolar amounts of the diaminopyridine and an alkali metal $C_{1-3}$ alkyl xanthate preferably potassium ethyl xanthate in a lower alkanol containing a little water and heating at 50° C. to reflux for 2-6 hours. The product can be isolated by making the mixture alkaline, filtering and neutralizing the filtrate.

The key intermediate in most of the above-described processes is the diaminopyridine, and it is prepared by the following process:

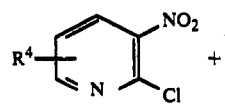

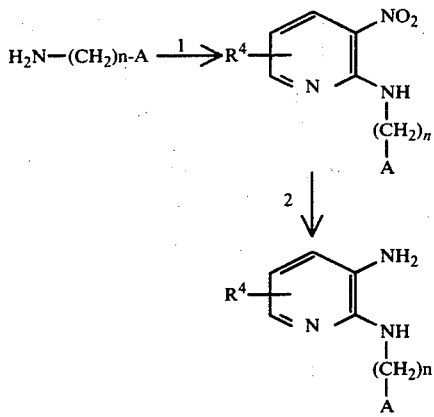

Step 1 of the above reaction scheme proceeds very readily, simply by heating a mixture of the chlornitropyridine and 2-3 equivalents of the amino compound, warming if necessary until an exothermic reaction ensues usually at about 80°-170° C., and, if necessary, controlling the temperature below about 250° C. for 10-60 minutes.

Because of the exothermic nature of the reaction, it is often found convenient to conduct it in the presence of a suitable organic solvent such as benzene, methanol, ethanol or acetic acid and the like, in the presence of an equimolar amount of sodium acetate until the condensation is complete, usually requiring 2 to about 10 hours.

The condensation may also be performed in a refluxing high boiling solvent such as dimethyl formamide in the presence of an acid acceptor such as an alkali metal carbonate and copper powder to catalyze the reaction.

Step 2 in the synthesis of the key intermediate comprises catalytic reduction of the nitro group with hydrogen in the presence of a hydrogenation catalyst, such as platinum or palladium in a lower alkanol, or Raney nickel in an alcohol or in alcoholic acetic acid. The resulting diaminopyridine is often very susceptible to air oxidation, turning black very quickly. In practice, it is therefore advisable to quickly add an excess of a mineral acid especially hydrochloric acid, to the filtrate after separation of the catalyst. Because of this instability, the key intermediate diaminopyridine acid addition salt is frequently not isolated, but rather held in acid solution and used as such in the final process for conversion to the imidazopyridines of this invention.

The novel compounds of this invention are potent analgesic agents as measured by the modified Randall Selitto test (Winter et al., *J. Pharmacol. Exptl. Ther.*, 150, 165–171 (1965)) which is known to correlate well with activity in mammals. They are also antiinflammatory and antipyretic agents.

It is therefore an object of the present invention to provide a method of treating pain and/or inflammation and/or fever with the novel compounds of this invention by the administration of active compound at the rate of 0.5 to 50 mg./kg./day, preferably from 4–15 mg./kg./day in a suitable pharmaceutical formulation, which is another embodiment of this invention, adapted for oral, topical, parenteral, inhalation or rectal administration.

The pharmaceutical formulations for oral use may be in the form of tablets, troches, lozenges, aqueous or oral suspensions, dispersible powders or granules, emulsions, hard or soft capsules, syrups or elixirs and may be prepared according to methods known in the art for the manufacture of such compositions.

The pharmaceutical formulations for rectal use are in the form of suppositories prepared according to art recognized methods.

For topical use, creams, ointments, gels, solutions or suspensions are employed.

The amount of active ingredient combined with the carrier materials of the pharmaceutical formulations to produce a single dosage form will vary depending on the mode of administration. For example, oral preparations should comprise from 5-500 mg., and preferably about 50-250 mg. of active compound in combination with the carrier materials.

EXAMPLE 1

1,3-Dihydro-3-(3,4-methylenedioxyphenyl)imidazo[4,5-b]pyridin-2-one

Step A: Preparation of 2-(3,4-methylenedioxyanilino)-3-nitropyridine

A mixture of 6.3 g. (0.04 mole) of 2-chloro-3-nitropyridine, 6.8 g. (0.05 mole) 3,4-methylenedioxyaniline and 4.1 g. (0.05 mole) of sodium acetate in 125 ml. of acetic acid was stirred and refluxed for 5 hours. The reaction mixture was concentrated to about ¼ of the original volume and diluted with 100 ml. of water. The precipitate was collected (11.5 g.) and a sample was recrystallized from ethanol to give 2-(3,4-methylenedioxyanilino)-3-nitropyridine, m.p. 146°-148° C.

Step B: Preparation of 3-amino-2-(3,4-methylenedioxyanilino)pyridine

The crude nitro compound from Step A (11.5 g.) was hydrogenated in 175 ml. of methanol using 0.5 g. of 5% palladium on carbon as catalyst, the theoretical amount of hydrogen being consumed in 16 hours. The catalyst was removed on a filter. The filtrate was concentrated in vacuo and the dark residue was extracted with 75 ml. of 2.5 N hydrochloric acid and 75 ml. of water. The crude solution was used directly in the next step.

Step C: Preparation of 1,3-dihydro-3-(3,4-methylenedioxyphenyl)imidazo[4,5-b]pyridin-2-one About ⅓ of the acid solution from Step B (i.e. about 4 gm. of the product) was treated with phosgene gas for 30 mins. and the dark solution was allowed to stand at room temperature overnight. Ammonium hydroxide was added dropwise with stirring to the ice-cold reaction mixture until alkaline. The precipitate was collected and extracted with 50 ml. of 2.5 N sodium hydroxide solution. The alkaline solution was treated with decolorizing charcoal and the filtrate therefrom was acidified with acetic acid. The precipitate (1.1 g.) was collected and recrystallized from dimethyl formamide-ether to give 900 mg. of 1,3-dihydro-3-(3,4-methylenedioxyphenyl)imidazo[4,5-b]pyridin-2-one, m.p. 256°-258° C.

Employing the procedure substantially as described in Example 1, but substituting for the 3,4-methylenedioxyaniline used in Step A thereof, an equimolar amount of an amino compound of formula:

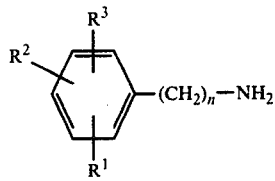

followed by reduction substantially as described in Step B, followed by treatment with phosgene substantially as described in Step C, there are produced respectively the nitroaminopyridines, diaminopyridines, and 1,3-dihydroimidazo[4,5-b]pyridine-2-ones described in Table I in accordance with the following equation:

EQUATION I

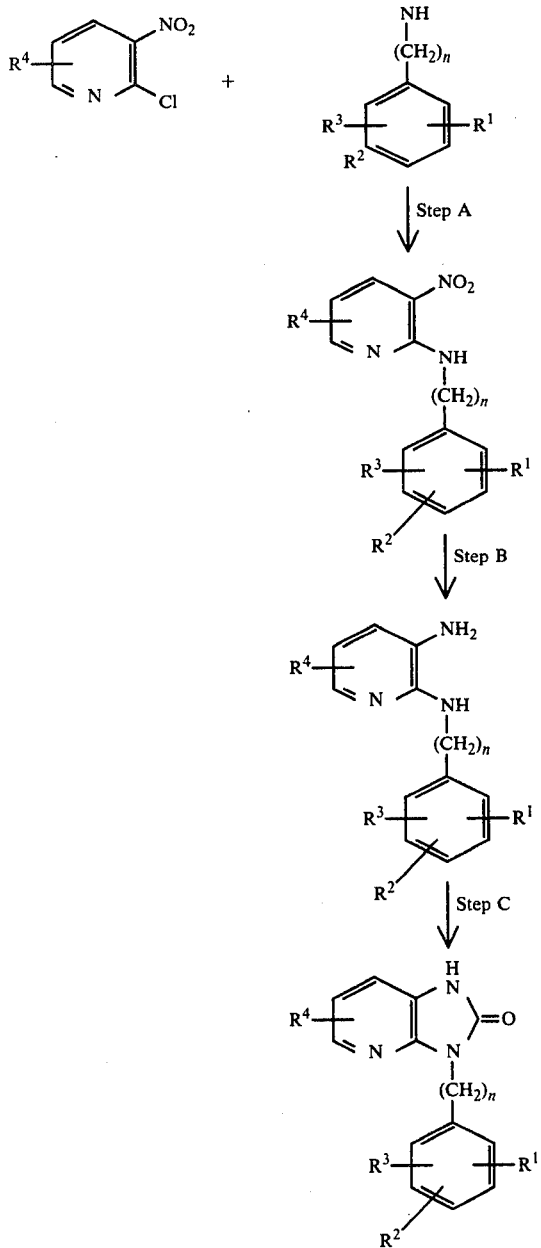

Table 1

| $R^1$ | $R^2$ | $R^3$ | $R^4$ | n | m.p. (° C) nitro-anilino-pyridine | m.p. (° C) final product |
|---|---|---|---|---|---|---|
| 2-OCH$_3$ | 4-OCH$_3$ | H | H | 0 | 139–140 | 204–206 |
| 3-O—(CH$_2$)$_2$—O-4 | | H | H | 0 | 126–127 | 267–269 |
| 3-OCH$_3$ | 4-OCH$_3$ | H | H | 0 | 97–98 | 245–246 |
| 2-OCH$_3$ | 5-OCH$_3$ | H | H | 0 | 145–147 | 243–244 |
| 3-CH$_3$ | 4-CH$_3$ | H | H | 0 | 134–136 | 188–190 |
| 3-OCH$_3$ | 4-OCH$_3$ | 5-OCH$_3$ | H | 0 | 139–140 | 265–266 |
| 3-OCH$_3$ | 4-CH$_3$ | H | H | 0 | 101–102 | 237–239 |
| 3-(CH$_2$)$_3$-4 | | H | H | 0 | 103–104 | 179–180 |

EXAMPLE 2
3-(3-Chloro-2-methylphenyl)-1,3-dihydroimidazo[4,5-b]pyridin-2-one Step A: Preparation of
2-(3-chloro-2-methylanilino)-3-nitropyridine A mixture of 6.3 g. (0.04 mole) of 2-chloro-3-nitropyridine and 16.9 g. (0.12 mole) of 3-chloro-2-methylaniline was heated in an oil bath to 170° C. when the temperature spontaneously rose to 185° C. After an additional 10 minutes at 180° C., the mixture was cooled to 50° C. and extracted with a solution of 75 ml. of water and 25 ml. of acetic acid. The insolubles were collected, air dried, dissolved in methylene chloride, and the solution was dried over magnesium sulfate. The solution was concentrated to a small volume and diluted with 50 ml. of ether which caused crystallization of 6.6 g. of 2-(3-chloro-2-methylanilino)-3-nitropyridine, m.p. 134°–135° C.

Step B: Preparation of
3-amino-2-(3-chloro-2-methylanilino)pyridine

The nitro compound (6.5 g.) from Step A was hydrogenated over 3 hours in 150 ml. of methanol in the presence of 1 teaspoon of Raney nickel catalyst. The catalyst was removed by filtration and 75 ml. of 2.5 N hydrochloric acid was added and the solution was treated with decolorizing charcoal.

Step C: Preparation of
3-(3-chloro-2-methylphenyl)-1,3-dihydroimidazo[4,5-b]pyridin-2-one The acid solution obtained in Step B was treated with phosgene as described in Example 1, Step C, to provide 3-(3-chloro-2-methylphenyl)-1,3-dihydroimidazo[4,5-b]pyridin-2-one, m.p. 224°–225° C.

Employing the procedure substantially as described in Example 2, but substituting for the 3-chloro-2-methylaniline used in Step A thereof an equimolar amount of a compound of formula:

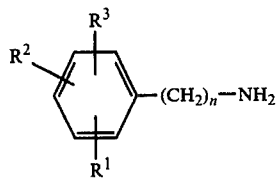

followed by reduction substantially as described in Step B, followed by treatment with phosgene substantially as described in Step C, there are produced respectively the nitroaminopyridines, diaminopyridines, and 1,3-dihydroimidazo[4,5-b]pyridine-2-ones described in Table II in accordance with Equation I.

Table II

| R¹ | R² | R³ | R⁴ | n | m.p. (° C) nitro-anilino-pyridine | m.p. (° C) final product |
|---|---|---|---|---|---|---|
| 3-CN | H | H | H | 0 | 155–157 | — |
| 3-O—CH₂—O-4 | | H | H | 1 | 113–115 | 236–238 |
| 2-CH₃ | 4-CH₃ | H | H | 0 | 121–125 | 110–112 |
| 2-Br | H | H | H | 0 | 138–140 | 240–243 |
| 2-F | 4-F | H | H | 0 | 114–116 | 240–242 |
| 3-F | H | H | H | 0 | 102–104 | 224 |
| 3-CF₃ | H | H | H | 0 | 81–82 | 177–178 |
| 4-F | H | H | H | 0 | 130–131 | 271–272 |
| 2-F | 5-CH₃ | H | H | 0 | 114–117 | 206–208 |
| 4-OCH₃ | H | H | H | 0 | 78–80 | 257–258 |
| 4-Cl | H | H | H | 0 | 146–147 | 267–269 |
| H | H | H | H | 0 | 71–73 | 240–241 |

EXAMPLE 3

3-(2-Methoxyphenyl)-1,3-dihydroimidazo[4,5-b]pyridin-2-one

Step A: Preparation of 2-(2-methoxyanilino)-3-nitropyridine

A mixture of 15.9 g. (0.10 mole) of 2-chloro-3-nitropyridine, 12.3 g. (0.10 mole) of 2-methoxyaniline, 8.2 g. (0.10 mole) of sodium acetate in 300 ml. of acetic acid was refluxed 1 hour. The mixture was concentrated in vacuo and the residue was diluted with water. The precipitate was collected (18.1 g.). The solids were boiled with 80 ml. of ethanol. The insoluble material was collected to give 13.7 g. of 2-(2-methoxyanilino)-3-nitropyridine, m.p. 151°–153° C.

Step B: Preparation of 2-(2-methoxyanilino)-3-aminopyridine hydrochloride

The nitro compound (13.7 g.) from Step A was hydrogenated in 300 ml. of ethanol over ¼ teaspoon of Raney nickel with hydrogen for 18 hours. The catalyst was removed on a filter and hydrogen chloride gas was bubbled into the filtrate for several minutes. Ether was added to complete crystallization of 10.5 g. of 2-(2-methoxyanilino)-3-aminopyridine hydrochloride, m.p. 260° C.

Step C: Preparation of 3-(2-methoxyphenyl)-1,3-dihydroimidazo[4,5-b]pyridin-2-one The amino compound (10 g.) from Step B was suspended in 75 ml. of ethanol, warmed on a steam bath and treated with enough water to cause solution. After decolorization with charcoal, the solution was treated with phosgene gas for 30 minutes. The solution allowed to evaporate partially in an open dish and then treated with excess ammonium hydroxide. The solids were collected and recrystallized from 100 ml. of ethanol to give 3.6 g. of 3-(2-methoxyphenyl)-1,3-dihydroimidazo[4,5-b]pyridin-2-one, m.p. 130° C. resolidifying and melting at 180° C.

Employing the procedure substantially as described in Example 3, but substituting for the 2-methoxy-aniline used in Step A thereof an equimolar amount of a compound of formula:

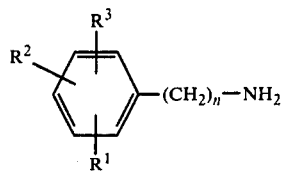

followed by reduction substantially as described in Step B, followed by treatment with phosgene substantially as described in Step C, there are produced respectively the nitroaminopyridines, diaminopyridines, and 1,3-dihydroimidazo[4,5-b]pyridin-2-ones described in Table III in accordance with Equation I.

Table III

| R¹ | R² | R³ | R⁴ | n | m.p. (° C) nitro-anilino-pyridine | m.p. (° C) final product |
|---|---|---|---|---|---|---|
| 4-CH₃ | H | H | H | 0 | 147–149 | 222–224 |
| 2-F | H | H | H | 0 | 102–103 | 199–200 |

EXAMPLE 4

3-(2,5-Difluorophenyl)-1,3-dihydroimidazo[4,5-b]pyridin-2-one

Step A: Preparation of 2-(2,5-difluoroanilino)-3-nitropyridine

A mixture of 5 g. (0.0315 mole) of 2-chloro-3-nitropyridine and 12.9 g. (0.1 mole) of 2,5-difluoroaniline was heated in an oil bath and under nitrogen to 120° C. when the temperature rose spontaneously to 160° C. It was heated further to 180° C. and held there for 10 minutes. After cooling slightly there was added 50 ml. of a 50% aqueous acetic acid solution. The precipitate was collected, dissolved in 75 ml. of hot benzene, filtered, concentrated to about 25 ml. and crystallized by addition of petroleum ether to give 6.8 g. of 2-(2,5-difluoroanilino)-3-nitropyridine, m.p. 150–152° C.

Step B: Preparation of 3-amino-2-(2,5-difluoroanilino)pyridine hydrochloride

The nitro compound (6.5 g.) from Step A was hydrogenated in 150 ml. of methanol over 0.35 g. of 5% platinum on carbon with hydrogen for 25 minutes. The catalyst was removed by filtration, and the filtrate was evaporated in vacuo. The residue was dissolved in 75 ml. of 2.5 N hydrochloric acid and 50 ml. of water. After standing at room temperature, the product crystallized to give 5.5 g. of 3-amino-2-(2,5-difluoroanilino)-pyridine hydrochloride.

Step C: Preparation of 3-(2,5-difluorophenyl)-1,3-dihydroimidazo[4,5-b]pyridin-2-one A suspension of 2 g. of the product from Step B in 75 ml. of water was treated with phosgene gas over 35 minutes, filtered, and allowed to stand at room temperature for 3 hours. The solution was treated with excess ammonium hydroxide. The precipitate (1.5 g.) was collected, dissolved in 25 ml. of hot dioxane and diluted with a little petroleum ether to give 1.3 g. of 3-(2,5-difluorophenyl)-1,3-dihydroimidazo[4,5-b]pyridin-2-one, m.p. 229° C.

Employing the procedure substantially as described in Example 4 but substituting for the 2,5-difluoroaniline used in Step A thereof an equimolar amount of an amine of structure:

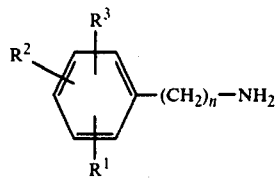

described in Table IV, followed by reduction substantially as described in Step B, optionally with an equal weight of 5% palladium on carbon as catalyst, followed by treatment with phosgene substantially as described in Step C, there are produced respectively the nitroaminopyridines, diaminopyridines, and imidazo[4,5-b]pyridin-2-ones described in Table IV in accordance with Equation I.

Table IV

| $R^1$ | $R^2$ | $R^3$ | $R^4$ | n | m.p. (° C) nitro-anilino-pyridine | m.p. (° C) final product |
|---|---|---|---|---|---|---|
| 2-N(CH$_3$)$_2$ | H | H | H | 0 | — | 222–224 |
| H | H | H | H | 2 | 86–87 | 163–164 |
| 2-Cl | 4-Cl | H | H | 0 | 144–145 | 172–174 |
| 2-F | 6-F | H | H | 0 | 114–116 | 252–253 |
| 4-C$_2$H$_5$ | H | H | H | 0 | 83–84 | 214–215 |
| 4-NH$_2$+ | H | H | H | 0 | 176–177++ | 301 |
| 2-Cl | H | H | H | 0 | 128–129 | 242–244 |
| 2-CH$_3$ | 6-CH$_3$ | H | H | 0 | 114–115 | 236–239 |
| 2-O—C$_3$H$_7$ | H | H | 0 | 0 | 96–98 | 202–204 |
| 3-Cl | 4-Cl | H | H | O | 167–168 | 282 |
| 4-OC$_6$H$_5$ | H | H | H | 0 | 105–107 | 236–237 |
| 3-OCH$_3$ | H | H | H | O | 98–100 | 196–198 |
| 3-OC$_6$H$_5$ | 0 | H | H | 0 | 81–82 | 188–190 |
| 2-F | H | H | 6-CH$_3$ | 0 | 111–113 | 183–184 |
| 2-F+++ | H | H | H | 1 | 116–118 | 191–192 |
| 4-COCH$_3$ | H | H | H | 0 | 155–157 | — |

` The starting material was H$_2$N—⟨ ⟩—NHCOCH$_3$.

The —COCH$_3$ group was hydrolyzed either during reduction of the nitro compound or the ring closure.
`` The structure of this product is

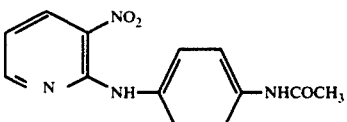

``` The nitro-benzylamino pyridine (m.p. 116–118) was prepared in benzene solution to moderate the rate of reaction.

EXAMPLE 5

3-(2-Fluorophenyl)-1,3-dihydroimidazo[4,5-b]pyridin-2-one

Step A: Preparation of 2-(2-fluoroanilino)-3-nitropyridine

A mixture of 15.9 g. (0.10 mole) of 2-chloro-3-nitropyridine, 22.2 g. (0.20 mole) of 2-fluoroaniline, 15.2 g. (0.12 mole) of potassium carbonate, 25 mg. of copper powder and 140 ml. of dimethyl formamide was refluxed for 2½ hours. The cooled mixture was poured into excess ice-water and the dark precipitate was collected and air dried. The solids were extracted with 100 ml. of boiling methylene dichloride. The extract was filtered, concentrated to a small volume to give 9.5 g. of 2-(2-fluoroanilino)-3-nitropyridine, m.p. about 97° C.

After recrystallization from ethanol it had m.p. 102°–103° C.

Step B: Preparation of 3-amino-2-(2-fluoroanilino)pyridine hydrochloride

The nitro compound (7 g.) from Step A was hydrogenated in 150 ml. of ethanol over one-fourth teaspoon of Raney nickel for 3 hours. The catalyst was removed on a filter and an excess of hydrogen chloride gas was bubbled into the filtrate. Ether was added to incipient cloudiness, and the solution was filtered. Addition of more ether caused crystallization of 2.7 g. of 3-amino-2-(2-fluoroanilino)pyridine hydrochloride, m.p. 225°–227° C.

Step C: Preparation of 3-(2-fluorophenyl)-1,3-dihydroimidazo[4,5-b]pyridin-2-one The product from step B (1.5 g.) was dissolved in 40 ml. of water and treated with phosgene as described in Example 1, Step C, to provide 3-(2-fluorophenyl)-1,3-dihydroimidazo[4,5-b]pyridin-2-one, m.p. 199°–200° C.

Employing the procedure substantially as described in Example 5, but substituting for the 2-fluoroaniline used in Step A thereof an equimolar amount of 4-chloroaniline followed by reduction substantially as described in Step B, followed by treatment with phosgene substantially as described in Step C, there are produced respectively:

2-(4-chloroanilino)-3-nitropyridine, m.p. 145°–147° C.;
3-amino-2-(4-chloroanilino)pyridine hydrochloride; and
3-(4-chlorophenyl)-1,3-dihydroimidazo[4,5-b]pyridin-2-one, m.p. 267°–269° C.

EXAMPLE 6

3-(2-Fluorophenyl)-1,3-dihydroimidazo[4,5-b]pyridin-2-one

A mixture of 2.7 g. of 3-amino-2-(2-fluoroanilino)pyridine hydrochloride (from Example 5, Step B) and 3 g. of urea was heated at 180° C. for 25 minutes. After cooling, the residue was stirred with 50 ml. of 2.5 N sodium hydroxide solution. The alkaline solution was treated with decolorizing charcoal and filtered. The filtrate was made acid and acetic acid which caused crystallization of product (1 g., m.p. 195° C.). This was recrystallized from ethylacetate-petroleum ether to give 800 mg. of 3-(2-fluorophenyl)-1,3-dihydroimidazo[4,5-b]pyridin-2-one, m.p. 199°–202° C.

EXAMPLE 7

3-Phenyl-1,3-dihydroimidazo[4,5-b]pyridin-2-one

Step A: Preparation of 2-chloro-3-(3-phenylureido)pyridine

A solution of 6 g. (9.05 mole) of phenylisocyanate in 25 ml. of toluene was added to a solution of 6.4 g. (0.05 mole) of 3-amino-2-chloropyridine in 100 ml. of toluene. The mixture was heated on a steam bath for 30 minutes and then evaporated to dryness. The residue was washed with ether and recrystallized from ethanol-petroleum ether to give 6.1 g. of 2-chloro-3-(3-phenylureido)pyridine, m.p. 178°–180° C.

Step B: Preparation of 3-phenyl-1,3-dihydroimidazo[4,5-b]pyridin-2-one

A mixture of 5.7 g. (0.023 mole) of the product from Step A, 3.45 g. (0.025 mole) of potassium carbonate, 20 mg. of copper powder and 50 ml. of dimethyl formamide was refluxed for 2½ hours. The cooled mixture was filtered and the solvent was evaporated in vacuo. The oily residue was extracted with 100 ml. of 1 N. sodium hydroxide solution and the extract was treated with decolorizing charcoal and filtered. The filtrate was neutralized with acetic acid. The crystalline precipitate of 600 mg. of 3-phenyl-1,3-dihydroimidazo[4,5-b]pyridin-2-one, m.p. 233°–235° C. was collected.

EXAMPLE 8

1,3-Dihydro-3-(2-methyl-6-pyridyl)imidazo[4,5-b]pyridin-2-one

Step A: Preparation of 2-(2-methyl-6-pyridylamino)-3-nitropyridine

A mixture of 4.0 g. of 2-chloro-3-nitropyridine and 5.5 g. 2-amino-6-methylpyridine was heated on an oil bath slowly to 175° C. The hot reaction mixture was decanted to a beaker causing crystallization. The solid mass was triturated with water, and the solids (6 g.) were collected. Recrystallization from about 100 ml. of hot ethanol gave 2.5 g. of 2-(2-methyl-6-pyridylamino)-3-nitropyridine, m.p. 153°–154° C.

Step B: Preparation of 3-amino-2-(2-methyl-6-pyridylamino)pyridine

The nitro compound (2.3 g.) from Step A was hydrogenated in 100 ml. of methanol over 0.4 g. of 5% palladium on carbon catalyst. The catalyst was removed by filtration and the filtrate was concentrated to dryness.

Step C: Preparation of 1,3-dihydro-3-(2-methyl-6-pyridyl)imidazo[4,5-b]pyridin-2-one The product from Step B (3.0 g.) was suspended in 60 ml. of 2.5 N hydrochloric acid, and the solution was treated with phosgene for 30 minutes. After standing 2 hours at room temperature, excess ammonium hydroxide was added. The precipitate was collected and recrystallized from 20 ml. of ethanol to give 2.0 g. of 1,3-dihydro-3-(2-methyl-6-pyridyl)imidazo[4,5-b]pyridin-2-one, m.p. 217°–219° C.

Employing the procedure of Example 8, Steps A through C, but substituting for the 2-amino-6-methylpyridine used in Step A thereof, an equimolar amount of cyclohexylamine, there is produced in sequence:
2-(cyclohexylamino)-3-nitroyridine (oil);
3-amino-2-(cyclohexylamino)pyridine.HCl (not isolated); and
3-cyclohexyl-1,3-dihydroimidazo[4,5-b]pyridin-2-one, m.p. 225°–226° C.

EXAMPLe 9

1,3-Dihydro-3-(2,2-dimethyl-1,3-benzodioxal-5-yl)imidazo-4,5-b]pyridin-2-one

Step A: Preparation of 5-amino-2,2-dimethyl-1,3-benzodioxole 2,2-Dimethyl-5-nitro-1,3-benzodioxole (m.p. 89°–91° C.) (13.5 g.) was hydrogenated in 250 ml. of methanol over 0.5 g. of 5% palladium on carbon for 2 hours. The catalyst was removed and the filtrate was evaporated to dryness. The residue was dissolved in benzene and again evaporated to dryness to give 11.6 g. of oily 5-amino-2,2-dimethyl-1,3-benzodioxole.

Step B: Preparation of 2-(2,2-dimethyl-1,3-benzodioxol-5-ylamino)-3-nitropyridine Prepared according to the process of Example 1, Step A, with:
2-chloro-3-nitropyridine (9.5 g.)
5-amino-2,2-dimethyl-1,3-benzodioxole (11.7 g.)
sodium acetate (5.6 g.)
acetic acid (200 ml.)
to give 11.5 g. of oil.

Step C: Preparation of 3-amino-2-(2,2-dimethyl-1,3-benzodioxol-5-ylamino)-pyridine hydrochloride Prepared according to the process of Example 1, Step B, with:
2-(2,2-dimethyl-1,3-benzodioxol-5-ylamino)-3-nitropyridine, (11.5 g.),
methanol (175 ml.)
5% Pd/C (0.5 g.)
2.5 N hydrochloric acid (125 ml.)
to give an acid solution used directly in the next step.

Step D: Preparation of 1,3-dihydro-3-(2,2-dimethyl-1,3-benzodioxol-5-yl)imidazo[4,5-b] pyridin-2-one Prepared according to the process of Example 1, Step C, with:
3-amino-2-(2,2-dimethyl-1,3-benzodioxol-5-ylamino)-pyridine hydrochloride (42 ml.)
phosgene (30 minutes)
to give 1,3-dihydro-3-(2,2-dimethyl-1,3-benzodioxol-5-yl)-imidazo[4,5-b]pyridin-2-one, m.p. 223°–224° C.

EXAMPLE 10

1,3-Dihydro-1-(2,3-dimethylbenzofuran-5-yl)imidazo[4,5-b]pyridin-2-one

Step A: Preparation of 2,3-dimethyl-5-aminobenzofuran 2,3-Dimethyl-5-nitrobenzofuran (13.4 g.) was hydrogenated in 200 ml. of methanol over 0.6 g. of 5% palladium on carbon. The catalyst was removed by filtration and the filtrate was evaporated to dryness to give 2,3-dimethyl-5-aminobenzofuran, m.p. 77°–78° C.

Step B: Preparation of 2-(2,3-dimethylbenzofuran-5-ylamino-3-nitropyridine

Prepared according to the process of Example 4, Step A, with:
2-chloro-3-nitropyridine (1.5 g.)
2,3-dimethyl-5-aminobenzofuran (3.0 g.)
reaction temperature 155° C.
to give 1.7 g. of 2-(2,3-dimethylbenzofuran-5-ylamino-3-nitropyridine, m.p. 114°–116° C.

Step C: Preparation of 3-amino-2-(2,3-dimethylbenzofuran-5-ylamino)pyridine

Prepared according to the process of Example 4, Step B, using:
2-(2,3-dimethylbenzofuran-5-ylamino)-3-nitropyridine (4.5 g.)
methanol (300 ml.)
5% Pd/C (0.5 g.)
to give 3-amino-2-(2,3-dimethylbenzofuran-5-ylamino)-pyridine, m.p. 168°–170° C.

Step D: Preparation of 1,3-dihydro-1-(2,3-dimethylbenzofuran-5-yl)imidazo[4,5-b]pyridin-2-one Prepared according to the process of Example 4, Step C, using:
3-amino-2-(2,3-dimethylbenzofuran-5-ylamino)pyridine (1 g.)
2.5 N hydrochloric acid (25 ml.)
phosgene (25 minutes)
to give 325 mg. of 1,3-dihydro-1-(2,3-dimethylbenzofuran-5-yl)imidazo[4,5-b]pyridin-2-one, m.p. 269°–270° C.

EXAMPLE 11

1,3-Dihydro-3-(2-fluorophenyl)-6-nitroimidazo[4,5-b]pyridin-2-one

Step A: Preparation of 3,5-dinitro-2-(2-fluoroanilino)pyridine

The temperature of a mixture of 2 g. of 2-chloro-3,5-dinitropyridine and 3 ml. of 2-fluoroaniline spontaneously rose to 80° C. and the mixture was then heated 15 minutes on a steam bath. The solid product was recrystallized from methanol to give 850 mg. of 3,5-dinitro-2-(2-fluoroanilino)pyridine, m.p. 159°–161° C.

Step B: Preparation of 2-(2-fluoroanilino)-3-amino-5-nitropyridine

A mixture of the product from Step A (1.0 g.) 15 ml. of ethanol and 5 ml. of concentrated ammonium hydroxide was warmed to 70° C. and hydrogen sulfide was bubbled in for 20 minutes. After cooling, the precipitate was collected and recrystallized from ethanol to give 2-(2-fluoroanilino)-3-amino-5-nitropyridine, m.p. 171°–172° C.

Step C: Preparation of 1,3-dihydro-3-(2-fluorophenyl)-6-nitroimidazo[4,5-b]pyridin-2-one The product from Step B (750 mg.) is dissolved in 150 ml. of benzene and treated with phosgene until reaction is complete. After standing 2 hours, the precipitate is collected and recrystallized from ethanol to give 1,3-dihydro-3-(2-fluorophenyl)-6-nitroimidazo[4,5-b]pyridin-2-one, m.p. 234°–236° C.

EXAMPLE 12

6-Amino-1,3-dihydro-3-(2-fluorophenyl)imidazo[4,5-b]pyridin-2-one

The product from Example 11 (205 mg.) was hydrogenated in 30 ml. of methanol over 25 mg. of 5% palladium on carbon. The catalyst was removed by filtration and the filtrate was concentrated to dryness to give 175 mg. of 6-amino-1,3-dihydro-3-(2-fluorophenyl)imidazo[4,5-b]pyridin-2-one, m.p. 220°–221° C.

EXAMPLE 13

1,3-Dihydro-3-(2-methyl-4,5-methylenedioxyphenyl)imidazo[4,5-b]pyridin-2-one

Step A: Preparation of 2-methyl-4,5-methylenedioxynitrobenzene

Piperonal (75 g.) was hydrogenated in 200 ml. of glacial acetic acid and 1 ml. of concentrated hydrochloric acid over 4 g. of 10% palladium on carbon. The catalyst was removed by filtration. The filtrate was cooled in acetone-dry ice and to it was added a mixture of 400 ml. of glacial acetic acid, 100 ml. of nitric acid (d=1.5) and 60 ml. of 70% nitric acid. After 1 hour in the cold, the mixture was allowed to warm to room temperature. It was poured onto ice and allowed to stand overnight. The precipitate was collected and recrystallized from 350 ml. of ethanol to give 57 g. of 2-methyl-4,5-methylenedioxynitrobenzene, m.p. 83°–84° C.

Step B: Preparation of 2-methyl-4,5-methylenedioxyaniline

The nitro compound (9.0 g.) from Step A was hydrogenated in 150 ml. of methanol over 500 mg. of 5% palladium on carbon for 30 minutes. The catalyst was removed by filtration, and the filtrate was evaporated to dryness. Recrystallization of the residue gave 4.5 g. of 2-methyl-4,5-methylenedioxyaniline, m.p. 88°–89° C.

Step C: Preparation of 2-(2-methyl-4,5-methylenedioxyanilino)-3-nitropyridine Prepared according to the process of Example 4, Step A, from:
2-chloro-3-nitropyridine (500 mg.)
2-methyl-4,5-methylenedioxyaniline (1.0 g.)
reaction temperature 150° C.
to give 500 mg. of 2-(2-methyl-4,5-methylenedioxyanilino)-3-nitropyridine, m.p. 167°–168° C.

Step D: Preparation of 3-amino-2-(2-methyl-4,5-methylenedioxyanilino)pyridine Prepared according to the process of Example 4, Step B, excluding the conversion to the hydrochloride salt from:
nitro compound from Step C (1.6 g.)
methanol (75 ml.)
5% palladium on carbon (0.4 g.)
to give 750 mg. of 3-amino-2-(2-methyl-4,5-methylenedioxyanilino pyridine, m.p. 180°–182° C.

Step E: Preparation of 1,3-dihydro-3-(2-methyl-4,5-methylenedioxyphenyl)imidazo[4,5-b]pyridin-2-one Prepared according to the process of Example 4, Step C, from:
amino compound from Step D (1.0 g.)
2.5 N hydrochloric acid (80 ml.)
phosgene (15 minutes)
to give 315 mg. of 1,3-dihydro-3-(2-methyl-4,5-methylenedioxyphenyl)imidazo[4,5-b]pyridin-2-one, m.p. 214°–215° C.

EXAMPLE 14

1,3-Dihydro-1-allyl-3-(3,4-methylenedioxyphenyl)imidazo[4,5-b]pyridin-2-one

To a suspension of 500 mg. (0.002 mole) of 1,3-dihydro-3-(3,4-methylenedioxyphenyl)imidazo[4,5-b]pyridin-2-one (from Example 1) in 50 ml. of acetone was added 220 mg. of powdered potassium hydroxide. After stirring 15 minutes, there was added 480 mg. (0.004 mole) of allylbromide. After 1 hour stirring at room temperature it was heated on a steam bath to boil away about half the solvent. Water was added to precipitate a solid which was collected on a filter (500 mg., m.p. about 100° C.). After recrystallization from benzene-petroleum ether there was obtained 400 mg. of 1,3-dihydro-1-allyl-3-(3,4-methylenedioxyphenyl)imidazo[4,5-b]pyridin-2-one, m.p. 130°–131° C.

Employing the procedure substantially as described in Example 14, but substituting for the allylbromide used therein, an equimolar amount of a compound R-hal, there are produced the 1,3-dihydro-1-R-3-($R^1R^2R^3$-phenyl)imidazo[4,5-b]pyridin-2-ones described in Table V in accordance with Equation II:

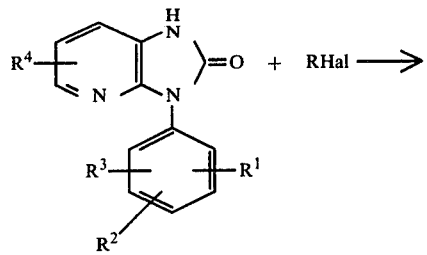

+ RHal ⟶

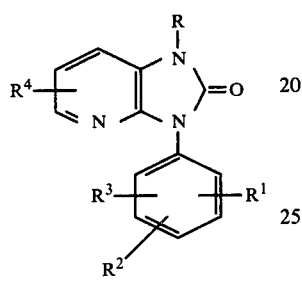

100 ml. of acetone and 140 mg. of powdered potassium hydroxide was stirred at room temperature 5 minutes and to it was added 960 ml. of 2,3-dichloropropene. The mixture was refluxed for 20 hours. Water (100 ml.) was added and after standing overnight it was collected on a filter (340 mg., m.p. 194°–195° C.). After recrystallization from 35 ml. of ethyl acetate there was obtained 170 mg. of 1-allenyl-1,3-dihydro-3-(3,4-methylenedioxyphenyl)imidazo[4,5-b]pyridin-2-one, m.p. 195°–196° C.

The filtrate from the 340 mg. obtained above, composed of an acetone-water solution was concentrated to remove the acetone. The remaining solution was extracted with 4 × 20 ml. of methylene chloride. The combined extracts were dried and concentrated to an oil. Trituration with hexane caused crystallization. Crystallization from ethyl acetate/hexane and from methanol gave 100 mg. of 1-(2-chloroallyl)-1,3-dihydro-3-(3,4-methylenedioxyphenyl)imidazo[4,5-b]pyridin-2-one, m.p. 122°–123° C.

EXAMPLE 16

1,3-Dihydro-1-ethoxycarbonylmethyl-3-(3,4-methylenedioxyphenyl)imidazo[4,5-b]pyridin-2-one and 1,3-Dihydro-1-carboxymethyl-3-(3,4-methylenedioxyphenyl)imidazo[4,5-b]pyridin-2-one To a stirred suspension of 2 g. (0.008 mole) of 1,3-

TABLE V

| $R^1$ | $R^2$ | $R^3$ | $R^4$ | R | Hal | m.p. |
|---|---|---|---|---|---|---|
| 3-O—$CH_2$—O-4 | | H | H | $C_6H_5$—$CH_2$— | Br | 111-113 |
| 3-O—$CH_2$—O-4 | | H | H | $(CH_3)_2CH$—$CH_2CH_2$— | Br | 91-93 |
| 3-O—$CH_2$—O-4 | | H | H | $CH_2$=C(CH$_3$)—$CH_2$— | Cl | 119-121 |
| 3-O—$CH_2$—O-4 | | H | H | HC≡C—$CH_2$— | Br | 207-209 |
| 3-O—$CH_2$—O-4 | | H | H | $C_6H_5(CH_2)_2$— | Br | 123-124 |
| 2F | H | H | H | $CH_2$=C=$CH_2$ | Br | 92-94 |
| 3-O—$CH_2$—O-4 | | H | H | $CH_3$ | I | 238-239 |
| 3-O—$CH_2$—O-4 | | H | H | cyclopropyl-$CH_2$— | Br | 141-142 |
| 3-O—$CH_2$—O-4 | | H | H | $(CH_3)_2C$=CH—$CH_2$— | Cl | 109-110 |
| 3-O—$CH_2$—O-4 | | H | H | cyclopropyl-C(=O)— | Cl | 192-193 |
| 3-O—$CH_2$—O-4 | | H | H | $CF_3SO_2$— | Cl | 155-156 |
| 3-O—$CH_2$—O-4 | | H | H | oxiranyl-$CH_2$—$CH_2$— | Br | 171-173 |
| 3-O—$CH_2$—O-4 | | H | H | $C_2H_5OOC$— | Cl | 191-192 |
| 3-O—$CH_2$—O-4 | | H | H | $C_6H_5CH$=C—$CH_2$— | Br | 161-162 |
| 3-O—$CH_2$—O-4 | | H | H | $C_6H_5C(O)CH_2$— | Br | 79-81+ |
| 3-O—$CH_2$—O-4 | | H | H | $HOCH_2CH_2$— | Br | 194-196 |
| 3-O—$CH_2$—O-4 | | H | H | 4-F—$C_6H_4$—$SO_2$— | Cl | 144-145 |
| 3-O—$CH_2$—O-4 | | H | H | $(CH_3)_2CHCH_2$— | Br | 124-126 |
| 3-O—$CH_2$—O-4 | | H | H | $C_6H_{11}$—$(CH_2)_2$— | Br | 103-104 |
| 3-O—$CH_2$—O-4 | | H | H | $CH_3(CH_2)_5$— | Br | 65-66 |
| 2-$CH_3$ | 3Cl | H | H | $CH_2$=CH—$CH_2$— | Br | 95-96 |
| 3-$OCH_3$ | 4-$OCH_3$ | H | H | $CH_2$=CH—$CH_2$— | Br | 120-121 |
| 3-$OCH_3$ | 4-$CH_3$ | H | H | $CH_2$=CH—$CH_2$— | Br | 104-105 |

+This product has 1 mole of acetone as solvate.

EXAMPLE 15

1-Allenyl-1,3-dihydro-3-(3,4-methylenedioxyphenyl)imidazo[4,5-b]pyridin-2-one and 1-(2-Chloroallyl)-1,3-dihydro-3-(3,4-methylenedioxyphenyl)imidazo[4,5-b]pyridin-2-one A mixture of 1.0 g. of 1,3-dihydro-3-(3,4-methylenedioxyphenyl)imidazo[4,5-b]pyridin-2-one, dihydro-3-(3,4-methylenedioxyphenyl)imidazo[4,5-b]pyridine-2-one in 100 ml. of acetone was added 980 mg. (0.016 mole) of powdered potassium hydroxide. After stirring at room temperature for 30 minutes 1.7 g. (0.01 mole) of ethyl bromoacetate was added over 3 minutes. After 3 hours at room temperature and 5 minutes on the steam bath, the acetone was evaporated. The residue was extracted with water (W) leaving 700 mg. of solid. Crystallization from benzene-petroleum ether gave 500 mg. of 1,3-dihydro-1-ethoxycarbonylmethyl-3-(3,4-methylenedioxyphenyl)imidazo[4,5-b]pyridin-2-one, m.p. 144°-146° C.

The water extract (W) from above was acidified with acetic acid. The precipitated solid (1 g.) was extracted with a solution of 50 ml. of water and 20 ml. of ammonium hydroxide. The extract was acidified with acetic acid. The precipitate was recrystallized from 60 ml. of alcohol to give 450 mg. of 1,3-dihydro-1-carboxymethyl-3-(3,4-methylenedioxyphenyl)imidazo[4,5-b]pyridin-2-one, m.p. 283° C.

EXAMPLE 17

1-Acetyl-3-(3,4-methylenedioxyphenyl)-1,3-dihydroimidazo[4,5-b]pyridin-2-one

A suspension of 500 mg. of 1,3-dihydro-3-(3,4-methylenedioxyphenyl)imidazo[4,5-b]pyridin-2-one in 15 ml. of acetic anhydride was heated on a steam bath overnight. The solution was evaporated in vacuo leaving a crystalline residue which was recrystallized from 20 ml. of benzene to give 1-acetyl-3-(3,4-methylenedioxyphenyl)-1,3-dihydroimidazo[4,5-b]pyridin-2-one, m.p. 211°-212° C.

EXAMPLE 18

1,3-Dihydro-3-(1,3-dihydro-5-isobenzofuranyl)imidazo[4,5-b]pyridin-2-one

Step A: Preparation of 5-nitrophthalan

Phthalan (6 g., 0.05 mole) was dissolved in 75 ml. of concentrated sulfuric acid, cooled to 5° C., and with stirring a solution of 5.1 g. (0.05 mole) of potassium nitrate in 25 ml. of concentrated sulfuric acid was added dropwise over 40 minutes while maintaining the temperature at <7° C. After an additional 30 minutes at ice-bath temperature and 30 minutes at room temperature, the solution was poured onto ice. The precipitate was collected and recrystallized from benzene-petroleum ether to give 5.5 g. of 5-nitrophthalan, m.p. 90°-92° C.

Step B: Preparation of 5-aminophthalan

The 5-nitrophthalan (19 g.) from Step A was hydrogenated in 200 ml. of methanol over 1 g. of 5% palladium on carbon for 30 minutes. The catalyst was removed by filtration and the filtrate was evaporated to dryness to give 15.1 g. of product, m.p. 102-104. Recrystallization from benzene-petroleum ether gave 5-aminophthalan, m.p. 104°-105° C.

Step C: Preparation of 2-(1,3-dihydro-5-isobenzofuranylamino)-3-nitropyridine Employing the procedure substantially as described in Example 3, Step A, but substituting for the 2-methoxyaniline used therein an equimolar amount of 5-aminophthalan, there is produced 2-(1,3-dihydro-5-isobenzofuranylamino)-3-nitropyridine, m.p. 146°-147° C.

Step D: Preparation of 3-amino-2-(1,3-dihydro-5-isobenzofuranylamino)pyridine The nitro compound (7.8 g.) from Step C was hydrogenated in 150 ml. of methanol over 0.5 g. of 5% palladium on carbon until close to the theoretical amount of hydrogen was absorbed. The catalyst was removed by filtration and the filtrate was diluted with an excess of 2.5 N hydrochloric acid. Most of the methanol was evaporated in vacuo and the residual solution was filtered.

Step E: Preparation of 1,3-dihydro-3-(1,3-dihydro-5-isobenzofuranyl)imidazo[4,5-b]pyridin-2-one Two-thirds of the acid solution from Step D was stirred and treated with phosgene for 45 minutes and allowed to stand at room temperature overnight. After treatment with decolorizing carbon, the solution was cooled in ice and there was added an excess of ammonium hydroxide. The precipitate was collected and stirred with 50 ml. of 2.5 N sodium hydroxide and filtered. The filtrate was acidified with acetic acid. The precipitate (1 g.) was collected (m.p. 243° C.) and recrystallized from 15 ml. dimethyl formamide by addition of ether to give 600 mg. of 1,3-dihydro-3-(1,3-dihydro-5-isobenzofuranyl)imidazo[4,5-b]pyridin-2-one, m.p. 248°-250° C.

EXAMPLE 19

1,3-Dihydro-3-(3,4-methylenedioxyphenyl)-1-propylimidazo[4,5-b]pyridin-2-one

1-Allyl-1,3-dihydro-3-(3,4-methylenedioxyphenyl)imidazo[4,5-b]pyridin-2-one (1 g.) was hydrogenated in 30 ml. of ethanol over 100 mg. of PtO$_2$ as catalyst for 1.5 hours. The mixture was warmed and the catalyst was removed by filtration. The filtrate was concentrated to a small volume. The crystalline product was collected and air dried to give 800 mg. of 1,3-dihydro-3-(3,4-methylenedioxyphenyl)-1-propylimidazo[4,5-b]pyridin-2-one, m.p. 112°-114° C.

EXAMPLE 20

1-Allyl-1,3-dihydro-3-(2-methylpyridin-6-yl)imidazo[4,5-b]pyridin-2-one

A mixture of 1 g. of 1,3-dihydro-3-(2-methylpyridin-6-yl)imidazo[4,5-b]pyridin-2-one in 100 ml. of acetone and 450 mg. of powdered potassium hydroxide was stirred 10 minutes and 1.1 g. of allyl bromide was added. After refluxing for 1.5 hours, the mixture was allowed to stand overnight at room temperature. The mixture was diluted with water and the acetone was evaporated causing crystallization of 325 mg. of 1-allyl-1,3-dihydro-3-(2-methylpyridin-6yl)imidazo[4,5-b]pyridin-2-one, m.p. 111°-112° C.

EXAMPLE 21

1,3-Dihydro-1-hydroxymethyl-3-(3,4-methylenedioxyphenyl)imidazo[4,5-b]pyridin-2-one A mixture of 500 mg. of 1,3-dihydro-3-(3,4-methylenedioxyphenyl)imidazo[4,5-b]pyridin-2-one and 30 ml. of 37% formaldehyde was heated on the steam bath for 1.5 hours. The hot solution was treated with decolorizing carbon, filtered, and the filtrate was treated with 2 ml. of 2.5 N sodium hydroxide and 30 ml. of water. The precipitate was collected: 400 mg. of 1,3-dihydro-1-hydroxymethyl-3-(3,4-methylenedioxyphenyl)imidazo[4,5-b]pyridin-2-one, m.p. 268° C.

EXAMPLE 22

1,3-Dihydro-3-(3,4-methylenedioxyphenyl)-2-oxoimidazo[4,5-b]pyridine-1-n-butylcarboxyamide A suspension of 1.2 g. of 1,3-dihydro-3-(3,4-methylenedioxyphenyl)imidazo[4,5-b]pyridin-2-one in 75 ml. of dry dimethoxyethane was treated with 1 g. of n-butyl isocyanate and refluxed until solution was complete. The solution was filtered and evaporated to near dryness and diluted with petroleum ether. The precipitate was recrystallized from 30 ml. of ethanol by addition of water to give 400 mg. of 1,3-dihydro-3-(3,4-methylenedioxyphenyl)-2-oxoimidazo[4,5-b]pyridine-1-n-butylcarboxamide,. m.p. 129°–130° C.

EXAMPLE 23

1,3-Dihydro-3-(3,4-methylenedioxyphenyl)-1-(2-thiazolinyl)imidazo[4,5-b]pyridin-2-one A suspension of 1.2 g. of 1,3-dihydro-3-(3,4-methylenedioxyphenyl)imidazo[4,5-b]pyridin-2-one in 100 ml. of dry dimethoxyethane was stirred and treated with 336 mg. of a 50% sodium hydride emulsion. After 15 minutes at room temperature, there was added 850 mg. of 2-chloroethylisothiocyanate and the mixture was refluxed 3 hours. Most of the solvent was evaporated and the residue was diluted with 40 ml. of 1 N sodium hydroxide. The precipitate was recrystallized from 5 ml. of dioxane-50 ml. of ether to give 450 mg. of 1,3-dihydro-3-(3,4-methylenedioxyphenyl)-1-(2-thiazolinyl)imidazo[4,5-b]pyridin-2-one, m.p. 224°–226° C.

EXAMPLE 24

1,3-Dihydro-3-(3,4-methylenedioxyphenyl)-1-(2-hydroxy-2-phenylethyl)imidazo[4,5-b]pyridin-2-one A mixture of 431 mg. of 1,3-dihydro-3-(3,4-methylenedioxyphenyl)-1-phenacylimidazo[4,5-b]pyridin-2-one in 30 ml. of methanol was hydrogenated over 25 mg. of platinum oxide. The catalyst was removed by filtration and the filtrate was evaporated to dryness to give a glass which could not be crystallized.

EXAMPLE 25

4-{[3-(1,3-benzodioxol-5-yl)-2-oxo-1H-imidazo[4,5-b]pyridine-1-(3H)yl]acetyl}morpholine A mixture of 600 mg. of 1,3-dihydro-2-oxo-3-(3,4-methylenedioxyphenyl)imidazo[4,5-b]pyridin-1-acetic acid and 10 ml. of thionyl chloride was heated on a steam bath for 3 hours. The mixture was evaporated to dryness and the residue was dissolved in ether and a slight excess of morpholine was added. The mixture was diluted with water and the precipitate was recrystallized from 10 ml. of methanol to give 100 mg. of 4-[3-(1,3-benzodioxol-5-yl)-2-oxo-1H-imidazo[4,5-b]pyridine-1-(3H)yl]acetyl morpholine, m.p. 212°–213° C.

EXAMPLE 26

1,3-Dihydro-3-(3,4-methylenedioxyphenyl)imidazo[4,5-b]pyridin-2-thione

A mixture of 2.6 g. (0.01 mole) of 3-amino-2-(3,4-methylenedioxyanilino)pyridine hydrochloride (Example 1, Step B), 1.8 g. (0.011 mole) of potassium ethyl xanthate, and 840 mg. (0.01 mole) of sodium bicarbonate in 45 ml. of ethanol and 10 ml. of water was heated at reflux for 3.5 hours. There was added 3 ml. of 2.5 N sodium hydroxide solution and the mixture was filtered. The filtrate was acidified with acetic acid and the precipitated product was collected (500 mg., m.p. 278° C.). After recrystallization from dioxane there was obtained 1,3-dihydro-3-(3,4-methylenedioxyphenyl)imidazo[4,5-b]pyridin-2-thione, m.p. 285° C.

Employing the procedure substantially as described in Example 26 but substituting for the 3-amino-2-(3,4-methylenedioxyanilino) pyridine hydrochloride, used therein an equimolar amount of the 3-amino-2-($R^1R^2$-anilino)pyridines described in Table VI, there are produced the 1,3-dihydroimidazo[4,5-b]pyridin-2-thiones also described in Table VI accordance with Equation III:

EQUATION III

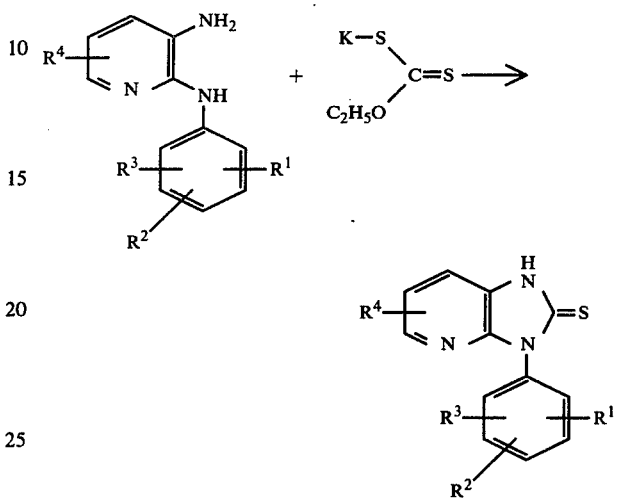

Table VI

| $R^1$ | $R^2$ | $R^3$ | $R^4$ |
|---|---|---|---|
| H | H | H | H |
| 2-F | H | H | H |

EXAMPLE 27

1,3-Dihydro-3-(2-fluorophenyl)imidazo[4,5-b]pyridin-2-thione

3-Amino-2-(2-fluoroanilino)pyridine hydrochloride (3 g.) is dissolved in 25 ml. of 2.5 N hydrochloric acid and treated with 2 ml. of thiophosgene. After stirring 3 hours the mixture is clarified by filtration, and the filtrate is neutralized with ammonium hydroxide. The product separates and is recrystallized from methanol to give 1,3-dihydro-3-(2-fluorophenyl)imidazo[4,5-b]pyridin-2-thione.

Employing the procedure substantially as described in Example 27 but substituting for the 3-amino-2-(2-fluoroanilino)pyridine hydrochloride used therein an equimolar amount of the diamines of structure:

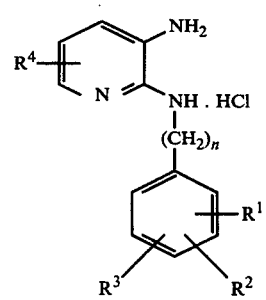

described in Table VII, there are produced the 1,3-dihydroimidazo[4,5-b]pyridines also described in Table VII in accordance with Equation IV.

Equation IV

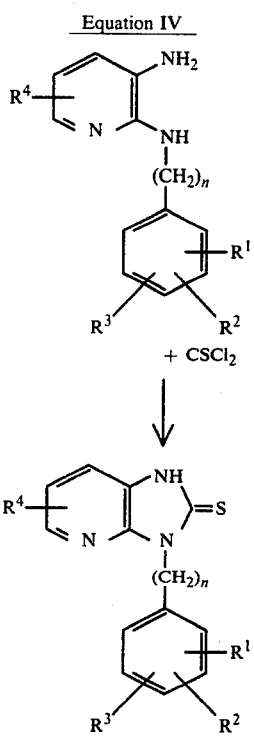

Table VII

| R¹ | R² | R³ | R⁴ | n |
|---|---|---|---|---|
| 3-O—CH₂—O-4 | | H | H | 0 |
| 2-OCH₃ | 4-OCH₃ | H | H | 0 |
| 3-O—(CH₂)₂—O-4 | | H | H | 0 |
| 3-OCH₃ | 4-OCH₃ | H | H | 0 |
| 2-OCH₃ | 5-OCH₃ | H | H | 0 |
| 3-CH₃ | 4-CH₃ | H | H | 0 |
| 3-OCH₃ | 4-OCH₃ | 5-OCH₃ | H | 0 |
| 3-OCH₃ | 4-CH₃ | H | H | 0 |
| 2-CH₃ | 3-Cl | H | H | 0 |
| 3-O—CH₂—O-4 | | H | H | 1 |
| 2-CH₃ | 4-CH₃ | H | H | 0 |
| 2-Br | H | H | H | 0 |
| 2-F | 4-F | H | H | 0 |
| 3-F | H | H | H | 0 |
| 3-CF₃ | H | H | H | 0 |
| 4-F | H | H | H | 0 |
| 2-F | 5-CH₃ | H | H | 0 |
| 4-OCH₃ | H | H | H | 0 |
| 4-Cl | H | H | H | 0 |
| H | H | H | H | 0 |
| 2-OCH₃ | H | H | H | 0 |
| 4-CH₃ | H | H | H | 0 |
| 2-F | 5-F | H | H | 0 |
| 2-N(CH₃)₂ | H | H | H | 0 |
| H | H | H | H | 2 |
| 2-Cl | 4-Cl | H | H | 0 |
| 2-F | 6-F | H | H | 0 |
| 4-C₂H₅ | H | H | H | 0 |
| 4-NH₂ | H | H | H | 0 |
| 2-Cl | H | H | H | 0 |
| 2-CH₃ | 6-CH₃ | H | H | 0 |
| 2-i-C₃H₇ | H | H | H | 0 |
| 3-Cl | 4-Cl | H | H | 0 |
| 4-OC₆H₅ | H | H | H | 0 |
| 3-OCH₃ | H | H | H | 0 |
| 3-OC₆H₅ | H | H | H | 0 |
| 2-F | H | H | 6-CH₃ | 0 |
| 2-F | H | H | H | 1 |
| 3-O—C(CH₃)(CH₃)—O-4 | | H | H | 0 |
| 3-CH₂—O—CH₂-4 | | H | H | 0 |
| 2-F | H | H | 6-NO₂ | 0 |
| 3-O—CH₂—O-4 | | 6-CH₃ | H | 0 |
| 3-(CH₂)₃-4 | | H | H | 0 |

EXAMPLE 29

(1) Tablets — 10,000 scored tablets for oral use, each containing 500 mg. of active ingredient are prepared from the following ingredients:

| | Gm. |
|---|---|
| 1-allyl-1,3-dihydro-3-(2-fluorophenyl)imidazo[4,5-b]pyridin-2-one | 5000 |
| Starch, U.S.P. | 350 |
| Talc, U.S.P. | 250 |
| Calcium Stearate | 35 |

The active ingredient is granulated with a 4% 2./v. aqueous solution of methylcellulose U.S.P. (1500 cps.). To the dried granules is added a mixture of the remainder of the ingredients and the final mixture compressed into tablets of proper weight.

(2) Capsules — 10,000 two-piece hard gelatin capsules for oral use, each containing 250 mg. of active ingredient are prepared from the following ingredients:

| | Gm. |
|---|---|
| 1,3-dihydro-3-(3,4-methylenedioxyphenyl)imidazo[4,5-b]pyridin-2-one | 2500 |
| Lactose, U.S.P. | 1000 |
| Starch, U.S.P. | 300 |
| Talc, U.S.P. | 65 |
| Calcium Stearate | 25 |

The active ingredient is mixed with the starch lactose mixture followed by the talc and calcium stearate. The final mixture is then encapsulated in the usual manner. Capsules containing 10, 25, 50 and 100 mg. of active ingredient are also prepared by substituting 100, 250, 500 and 1000 gm. for 2500 gm. in the above formulation.

(3) Soft elastic capsules — One-piece soft elastic capsules for oral use, each containing 500 mg. of active material are prepared in the usual manner by first dispersing the active material in sufficient corn oil to render the material capsulatable.

(4) Aqueous suspension — An aqueous suspension for oral use containing in each 5 ml., 250 mg. of active ingredient is prepared from the following ingredients:

| | Gm. |
|---|---|
| 1-allyl-1,3-dihydro-3-(3,4-methylenedioxyphenyl)imidazo-[4,5-b]pyridin-2-one | 5000 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D. & C. orange dye | 7.5 |
| Deionized water, q.s. to 10,000 ml. | |

(5) Gel Formulation —

0.1 mg. disodium edetate
1.30 mg. of purified H₂O
300 mg. isopropanol
26 mg. hydroxypropylcellulose
q.s.a.d. 1 gm. propylene glycol
50 mg. 1-allyl-1,3-dihydro-3-(3,4-methylenedioxyphenyl)imidazo[4,5-b]pyridin-2-one.

(6) Ointment Formulation —
50 mg. wood alcohols B.P.
150 mg. amichol C
350 mg. wax white Be square 170°/175° C.
50 mg. 1-allyl-,3-dihydro-3-(3,4-methylenedioxyphenyl)imidazo[4,5-b]pyridin-2-one
q.s.a.d. 1 gm. isopropyl myristate

EXAMPLE 30

1,3-Dihydro-1-isopropyl-3-(3,4-methylenedioxyphenyl)imidazo[4,5-b]pyridin-1-one

To a stirred suspension of 2.5 g. (0.01 mole) of 1,3-dihydro-3-(3,4-methylenedioxyphenyl)imidazo[4,5-b]-pyridin-2-one (from Example 1) in 150 ml. of acetone, was added 1.12 g. (0.02 mole) of powdered potassium hydroxide. After stirring 15 minutes, 2.46 g. (0.02 mole) of isopropyl bromide was added. The mixture was stirred for 15 minutes then heated on a steam bath for 16 hours. The mixture was concentrated to a small volume and then diluted with 25 ml. of 2.5 N sodium hydroxide and 100 ml. of water. An oil formed and solidified. It was removed and crystallized from benzene by the addition of petroleum ether to give crystals of the subject product melting at 175°–176° C.

EXAMPLE 31

1-Butyl-1,3-dihydro-3-(3,4-methylenedioxyphenyl)imidazo[4,5-b]pyridin-2-one

To a suspension of 2.6 g. (0.01 mole) of 1,3-dihydro-3-(3,4-methylenedioxyphenyl)imidazo[4,5-b]-pyridin-2-one in 150 ml. of acetone, was added 1.12 g. (0.02 mole) of powdered potassium hydroxide. The mixture was stirred at room temperature for 20 minutes and 2.74 g. (0.02 mole) of 1-bromobutane was added. The mixture was stirred at reflux for 16 hours and then evaporated in vacuo. The residue was extracted with a solution of 20 ml. of 2.5 N sodium hydroxide and 50 ml. of water. The product was separated by filtration and was purified by crystallization from ether-petroleum ether giving 2.4 g. of white needles melting at 74°–75° C.

The novel compounds of this invention wherein $R^4$ is halo or lower alkoxy carbonyl amino also may be prepared conveniently from the corresponding compounds wherein $R^4$ is amino. Treatment of such $R^4$ amino compounds with a lower alkyl halo formate, such as ethylchloroformate, methylchloroformate, propylchloroformate and the like, readily produces compounds wherein $R^4$ is lower alkoxy carbonylamino. Where compounds wherein $R^4$ is halo are desired, the $R^4$ amino compound is diazotized by treatment with an alkali metal nitrite, such as sodium or potassium nitrite, in the presence of a strong acid, such as hydrochloric acid. Addition of a halo boric acid, such as fluoro boric acid, to the resulting diazotized solution yields the desired $R^4$ halo compound.

EXAMPLE 32

6-Amino-1-n-propyl-1,3-dihydro-3-(3,4-methylenedioxyphenyl)imidazo[4,5-b]pyridin-2-one

STEP A:
2-(3,4-methylenedioxyanilino)-3,5-dinitropyridine

To a stirred solution of 12.0 g. (0.0875 mole) of 3,4-methylenedioxyaniline in 100 ml. of methanol, was added with stirring 8.0 g. (0.04 mole) of 2-chloro-3,5-dinitropyridine. Within one minute the mixture had crystallized. To complete the reaction, the mixture was heated on a steam bath for 15 minutes, then cooled and filtered to give 11.0 g. of product. A small amount recrystallized from methanol melted at 187°–188° C.

STEP B:
2-(3,4-Dimethylenedioxyanilino)-3-amino-5-nitropyridine

A stirred suspension containing 3.5 g. (0.0115 mole) of the dinitro product of Step A in 150 ml. of ethanol was heated to 50° C. and 20 ml. of concentrated ammonium hydroxide was added. Hydrogen sulfide was then bubbled into the mixture. A solution resulted but the addition was continued for 30 minutes. Upon cooling, a precipitate appeared and was removed by filtration. The separated preciptiate weighed 7.5 g. and contained sulfur, as well as, the desired product. After extraction with three 100 ml. portions of carbon disulfide, the residue melted at 211°–212° C.

STEP C
6-Nitro-1,3-dihydro-3-(3,4-methylenedioxyphenyl-)imidazo[4,5-b]pyridin-2-one A mixture of 2.0 g. (0.0073 mole) of the nitropyridine product of Step B with 10.0 g. of urea was heated in an oil bath with stirring at 200° C. for 15 minutes. After cooling, water was added to dissolve excess urea and the precipitate was removed by filtration. The precipitate was warmed in 1 N sodium hydroxide and clarified by filtration. The filtrate was neutralized with hydrochloric acid and the resulting precipitate was removed by filtration. This precipitate was dissolved in 350 ml. of boiling methanol, treated with charcoal and filtered. The filtrate was concentrated to about 50 ml. The product crystallized, weighed 900 mg. and melted at 224°–225° C.

STEP D
6-Nitro-1-allyl-1,3-dihydro-3-(3,4-methylenedioxyphenyl)imidazo[4,5-b]pyridin-2-one To a mixture of 1.1 g. (0.0036 mole) of the nitro product of Step C in 175 ml. of refluxing acetone, was added 400 mg. (0.0068 mole) of powdered potassium hydroxide. The mixture was stirred and heated for 15 minutes, 1 ml. of allyl bromide was added and reflux was continued for 1.5 hours. About 50 ml. of water was then added and the resulting solution was concentrated to about 75 ml. The product, 1.2 g. crystallized and melted at 152°–153° C.

STEP E
6-Amino-1-n-propyl-1,3-dihydro-3-(3,4-methylenedioxyphenyl)imidazo[4,5-b]pyridin-2-one The nitro product of Step D, 340 mg. (0.001 mole), in 30 ml. of methanol was hydrogenated in the presence of 50 mg. of 5% palladium on carbon. The theoretical amount of hydrogen was absorbed. The catalyst was removed by filtration and the filtrate was evaporated to give the product which was crystallized from benzene by addition of hexane, m.p. 177°–178° C.

EXAMPLE 33

6-Ethoxycarbonylamino-1-n-propyl-1,3-dihydro-3-(3,4-methylenedioxyphenyl)-imidazo[4,5-b]pyridin-2-one To 50 mg. of the amine prepared in Example 32 in 1 ml. of cold pyridine, was added a few drops of ethylchloroformate. After standing for 30 minutes, water was added and the resulting precipitate was recovered

EXAMPLE 34

6-Fluoro-1-n-propyl-1,3-dihydro-3-(3,4-methylenedioxyphenyl)imidazo[4,5-b]pyridin-2-one To a mixture of 936 mg. (0.003 mole) of the amine prepared in Example 32 in 12 ml. of 2.5 N. hydrochloric acid, cooled to 0° C., was added a solution containing 250 mg. (0.0035 mole) of sodium nitrite in 2 ml. of water. After stirring cold for 15 minutes, 3 ml. of a 40% fluoroboric acid was added slowly. There was an immediate precipitate. After stirring 1 hour, the precipitate (1.15 g.) was removed by filtration. This fluoroborate salt decomposed about 165°–175° C. This salt was mixed with 5 g. of sand and heated in an oil bath. When the bath reached 175°, boron trifluoride began to come off. The temperature of the bath finally reached 205° C. Total heating time between 175° and 205° was 15 minutes. The mixture was cooled, extracted with acetone, and the acetone evaporated in vacuo. The residue was shaken with 150 ml. of methylene dichloride and 2 ml. of saturated sodium bicarbonate solution. The aqueous solution was separated, and the methylene dichloride solution dried. The solvent was removed in vacuo, and the oil residue treated with benzene. A solid precipitate formed and was removed by filtration. The filtrate was evaporated in vacuo and ether was added. Another precipitate formed and was removed. After evaporating the ether, hexane was added to give a third precipitate, which was removed. Slow evaporation of the hexane yielded 50 mg. of crystals of 6-fluoro-1-n-propyl-1,3-dihydro-3-(3,4-methylenedioxyphenyl)imidazo[4,5-b]pyridin-2-one, which melted at 153°–154° C.

EXAMPLE 35

5-Amino-1-allyl-1,3-dihydro-3-(3,4-methylenedioxyphenyl)imidazo[4,5-b]pyridin-2-one

STEP A

6-Chloro-2-(3,4-methylenedioxyanilino)-3-nitropyridine

In 300 ml. of ethanol was dissolved 9.65 g. (0.05 mole) of 2,6-dichloro-3-nitropyridine, and 4.2 g. (0.05 mole) of sodium bicarbonate was added. The mixture was stirred at room temperature while a solution of 6.85 g. (0.05 mole) of 3,4-(methylenedioxy)aniline in 100 ml. of ethanol was added over 20 minutes. Stirring at room temperature was continued overnight. The mixture was concentrated to one-half volume, water was added; and the deep red solid product was collected by filtration. The product weighed 15.2 g. A small amount was purified by crystallization from ethanol. It melted at 160°–162° C.

STEP B:

3-Amino-6-chloro-2-(3,4-methylenedioxyanilino)pyridine

The nitropyridine product of Step A, 2.93 g., was hydrogenated in 50 ml. of ethylacetate in the presence of 0.3 g. of platinum oxide. After the calculated amount of hydrogen was absorbed, the catalyst was removed by filtration and the filtrate was evaporated in vacuo. The dark residue was rubbed with petroleum ether and the amino compound crystallized. The crude product weighed 2.5 g. and was purified by recrystallization from ethylacetate-petroleum ether and melted at 162°–163° C.

STEP C:

5-Chloro-1,3-dihydro-3-(3,4-methylenedioxyphenyl)imidazo[4,5-b]-pyridin-2-one

A mixture of 7.9 g. of the aminopyridine product of Step B and 25 g. of urea was heated in an oil bath at 185°–190° C. The reaction was kept at this temperature for 10 minutes then cooled and extracted with water. The crude product was extracted with 75 ml. of 2.5 N sodium hydroxide. The alkaline solution was treated with charcoal and excess acetic acid then was added to precipitate the product. The precipitate was purified by crystallization from dimethylformamide-ether.

STEP D:

1-Allyl-5-chloro-1,3-dihydro-3-(3,4-methylenedioxyphenyl)imidazo [4,5-b]pyridin-2-one To a stirred suspension of 4.6 g. (0.016 mole) of the imidazopyridine product of Step C in 175 ml. of acetone, was added 1.8 g. (0.032 mole) of powdered potassium hydroxide. After stirring at room temperature for 20 minutes, 3.9 g. (0.032 mole) of allylbromide was added. Stirring at room temperature was continued overnight and the mixture then was concentrated to one-half volume. The concentrate was diluted with 150 ml. of water and the crude product was collected by filtration. The crude product was crystallized from 70 ml. of ethanol giving 2.0 g. of needles melting at 146°–148° C.

STEP E:

1-Allyl-5-amino-1,3-dihydro-3-(3,4-methylenedioxyphenyl)imidazo-[4,5-b]pyridin-2-one Heat a mixture of 2.5 g. of the imidazopyridin product of Step D and 25 ml. of liquid ammonia in a bomb at 150° C. for 3 hours. Remove the excess ammonia and crystallize the residue from dimethyl formide-water.

EXAMPLE 36

5-Ethoxycarbonyl-1-allyl-1,3-dihydro-3-(3,4-methylendioxyphenyl)imidazo[4,5-b]pyridin-2-one Dissolve 1 g. of amino product produced in Example 35 in 20 ml. of dry pyridine. Cool in an ice-bath and stir while slowly adding 300 mg. of ethyl chloroformate. Allow the reaction mixture to stand at room temperature overnight. Pour the reaction mixture into ice-water and collect the crude product by filration. Crystallize the crude product from dimethyl formamide-ether.

EXAMPLE 37

5-Fluoro-1-allyl-1,3-dihydro-3-(3,4-methylenedioxyphenyl)imidazo[4,5-b]pyridin-2-one

STEP A: 2,6-difluoro-3-nitropyridine

To a stirred solution of 20 g. of 2,6-difluoropyridine in 100 ml. of concentrated sulfuric acid at about 20° C., was added 75 ml. of 90% fuming nitric acid over 20 minutes. The mixture was kept at room temperature overnight, warmed to 35° C. over 15 minutes and held at this temperature for 10 minutes. The solution was cooled and poured into ice. The oil was extracted with 400 ml. of ether and the ether extract was washed with bicarbonate solution until all of the acid was neutralized. The ether was dried, evaporated and the residue was distilled at 0.1 mm. The only fraction came over at 50° C.

STEP B:
6-Fluoro-2-(3,4-methylenedioxyanilino)-3-nitropyridine

In 75 ml. of ethanol was dissolved 3.2 g. (0.002 mole) of 2,6-difluoro-3-nitropyridine followed by 1.68 g. (0.02 mole) of sodium bicarbonate. To this stirred mixture, was added a solution of 2.74 g. (0.02 mole) of 3,4-(methylenedioxy) aniline in 50 ml. of ethanol dropwise over 45 minutes at room temperature. After one hour, 100 ml. of water was added and the deep-red crystalline solid product was collected. A small amount was crystallized from ethanol and melted at 161°-162° C.

STEP C:
3-Amino-6-fluoro-2-(3,4-methylene-dioxyanilino)pyridine

Hydrogenate the nitropyridine product from Step B, 3.0 g., in 75 ml. of ethylacetate in the presence of 0.3 g. of platinum oxide. After the theoretical amount of hydrogen is taken up, remove the catalyst by filtration and evaporate the filtrate in vacuo. Rub the residue with petroleum ether and crystallize the product from ethylacetate-petroleum ether.

STEP D:
1,3-Dihydro-5-fluoro-3-(3,4-methylenedioxyphenyl) imidazo[4,5-b]pyridin-2-one Heat a mixture of 2 g. of the aminopyridine product of Step C and 6 g. of urea at 185°-190° C. in an oil bath for 10 minutes. Cool and extract the reaction mixture with water. Extract the crude solid with 35 ml. of 2.5 N sodium hydroxide. Filter the alkaline solution and treat with excess acetic acid to precipitate the product. Crystallize from dimethyl formamide-ether.

STEP E:
5-Fluoro-1-allyl-1,3-dihydro-3-(3,4-methylenedioxyphenyl)imidazo[4,5-b]pyridin-2-one Treat a suspension of 1.4 g. (0.005 mole) of the imidazopyridine product of Step D in 80 ml. of acetone with 560 mg. (0.01 mole) of powdered potassium hydroxide. Stir at room temperature for 20 minutes and add 1.21 g. (0.01 mole) of allyl bromide. Continue stirring overnight. Concentrate the reaction mixture to one-half volume and dilute with 75 ml. of water. Separate the solid product by filtration and crystalize from ethanol.

EXAMPLE 38
1,3-Dihydro-1-cyclopentyl-3-(3,4-methylenedioxyphenyl)imidazo[4,5]-b]pyridin-2-one To a stirred suspension of 5 g. of 1,3-dihydro-3-(3,4-methylenedioxyphenyl)imidazo[4,5-b]pyridin-2-one in 350 ml. of acetone was added 2.2g. of powdered potassium hydroxide. After 30 minutes of stirring a solution resulted and there was then added 5 ml. of bromocyclopentane, after which the solution was heated under reflux for 20 hours. The resulting clear liquid was decanted from a small amount of solid and was concentrated under reduced pressure to about 50 ml. To this residue was added 150 ml. of methylene dichloride, and a solution of 15 ml. of 10% by weight sodium hydroxide and 35 ml. of water. After shaking, the organic layer was separated, dried over magnesium sulfate and concentrated to 25 ml. The addition of 100 ml. of hexane caused the slow crystallization of 1,3-dihydro-1-cyclopentyl-3-(3,4-methylenedioxyphenyl)imidazo[4,5-b]pyridin-2-one, m.p. 159°-162° C. The yield was 3.1 g.

EXAMPLE 39
1,3-Dihydro-1-methoxymethyl-3-(3,4-methylenedioxyphenyl) imidazo[4,5-b]pyridin-2-one To a stirred suspension of 3.82 g. of 1,3-dihydro-3-(3,4-methylenedioxyphenyl)imidazo[4,5-b]pyridin-2-one in 175 ml. of acetone was added 1.8g. of powdered potassium hydroxide, and after 20 minutes of stirring a solution resulted. To this solution was added 2.4 g. of chloromethylmethyl ether, and after stirring for 2 hours, the reaction mixture was allowed to evaporate in an evaporating dish. The solid residue was extracted with 25 ml. of 2.5N sodium hydroxide in 75 ml. of water, and the insoluble residue was dissolved in 100 ml. of methylene dichloride and dried. This solution was stirred with 5G. of aluminum oxide, filtered, and the filtrate evaporated to 20 ml. The addition of 75 ml. of ether caused the final product to crystallize. Yield of the final product was 2.8g., and it was found to have an m.p. of 152°-153° C.

What is claimed is:

1. The compound of the formula:

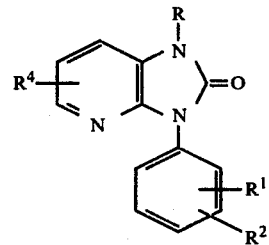

wherein
R is hydrogen; $C_{1-7}$ alkyl; $C_{2-6}$ alkenyl; $C_{1-7}$ alkyl substituted with $C_{3-6}$ cycloalkyl, $C_{1-5}$ alkoxy, or hydroxy, or $C_{4-7}$ cycloalkyl; $R^1$ and $R^2$ and $R^4$ is hydrogen; 5- or 6- fluoro; 5- or 6- chloro; or 5- or 6- $C_{1-5}$ alkoxy carbonylamino on adjacent carbon atoms taken together

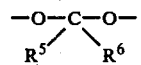

wherein $R^5$ and $R^6$ are hydrogen or lower alkyl.

2. The compound of claim 1 being 1-isopropyl-1,3-dihydro-3-(3,4-methylenedioxyphenyl)-imidazo[4,5-b]pyridin-2-one.

3. The compound of claim 1 being 1-butyl-1,3-dihydro-3-(3,4-methylenedioxyphenyl)-imidazo[4,5-b]pyridin-2-one.

4. The compound of claim 1 being 6-ethoxycarbonylamino-1-n-propyl-1,3-dihydro-3-(3,4-methylenedioxyphenyl-imidazo[4,5-pyridin-2-one.

5. The compound of claim 1 being 5-fluoro-1-allyl-1,3-dihydro-3-(3,4-methylenedioxyphenyl)imidazo[4,5-b]pyridin-2-one.

6. The compound of claim 1 being 6-fluoro-1-n-propyl-1,3-dihydro-3-(3,4-methylenedioxyphenyl-)imidazo[4,5b]pyridin-2-one.

7. The compound of claim 1 being 5-ethoxycarbonylamino-1-allyl-1,3-dihydro-3-(3,4-methylenedioxyphenyl)imidazo[4,5-b]pyridin-]-one.

8. The compound of claim 1 being 5-fluoro-1,3-dihydro-3-(3,4-methylenedioxyphenyl) imidazo[4,5-b]pyridin-2-one.

9. The compound of claim 1 being 1-n-propyl-1,3-dihydro-3-(3,4-methylenedioxyphenyl)imidazo[4,5-b]pyridin-2-one.

10. The compound of claim 1 being 1-methyl-1,3-dihydro-3-(3,4-methylenedioxyphenyl)imidazo[4,5-b]pyridin-2-one.

11. The compound of claim 1 being 1-ethyl-1,2-dihydro-/3-(3,4-methylenedioxyphenyl)imidazo[4.5-pyridin-2-one.

12. The compound of claim 1 being 1-cyclopropylmethyl-1,3-dihydro-3-(3,4-methylenedioxyphenyl)imidazo[4,5-b]pyridin-2-one.

13. The compound of claim 1 being 1-hydroxyethyl-1,3-dihydro-3-(3,4-methylenedioxyphenyl)imidazo[4,5-b]pyridin-2-one.

14. The compound of claim 1 being 1-cyclopentyl-1,3-dihydro-3-(3,4-methylenedioxyphenyl)imidazo[4,5-b]pyridin-2-one.

15. The compound of claim 1 being 1-methoxymethyl-1,3-dihydro-3-(3,4-methylenedioxyphenyl)imidazo[4,5-b]pyridin-2-one.

16. The compound of claim 1 being 5-chloro-1-allyl-1,3-dihydro-(3,4-methylenedioxyphenyl)imidazo[4,5-b]pyridin-2-one.

17. The compound of claim 1 being 1-allyl-1,3-dihydro-3-(3,4-methylenedioxyphenyl)imidazo[4,5-b]pyridin-2-one.

18. The compound of claim 1 being 1,3-dihydro-3-(3,4-methylenedioxyphenyl)imidazo[4,5-b]pyridin-2-one.

19. A method of treating pain and/or inflammation and/or fever which comprise the administration to a patient in need of such treatment an effective amount of a compound of formula:

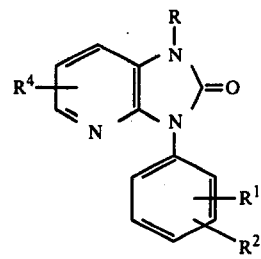

wherein
R is hydrogen; $C_{1-7}$ alkyl; $C_{2-6}$ alkenyl; substituted with $C_{3-6}$ cylcoalkyl, $C_{1-5}$ alkoxy, or hydroxy; or $C_{4-7}$ cycloalkyl;
$R^1$ and $R^2$ are hydrogen; fluoro; $C_{1-5}$ alkyl; or —O—$CH_2$—O— attached to adjacent carbon atoms; and $R^4$ is hydrogen; 5- or 6- fluoro; 5- or 6- chloro; or 5- or 6- $C_{1-5}$ alkoxy carbonylamino.

20. A pharmaceutical composition comprising a carrier and an effective amount of a compound of formula:

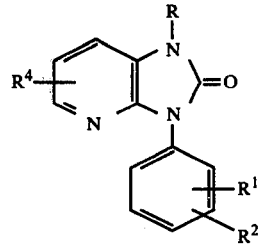

wherein
R is hydrogen; $C_{1-7}$ alkyl; $C_{2-7}$ alkenyl; substituted with $C_{3-6}$ cycloalkyl, $C_{1-5}$ alkoxy, or hydroxy; or $C_{4-7}$ cycloalkyl;
$R^1$ and $R^2$ are hydrogen; fluoro; $C_{1-5}$ alkyl; or —O—$CH_2$—O— attached to adjacent carbon atoms; and $R^4$ is hydrogen; 5- or 6- fluoro; 5- or 6- chloro; or 5- or 6- $C_{1-5}$ alkoxy carbonylamino.

* * * * *